(12) United States Patent
Furst et al.

(10) Patent No.: US 8,323,333 B2
(45) Date of Patent: Dec. 4, 2012

(54) FRAGILE STRUCTURE PROTECTIVE COATING

(75) Inventors: Joseph G. Furst, Lyndhurst, OH (US); William G. Brodbeck, Hudson, OH (US)

(73) Assignee: ICON Medical Corp., Cleveland, OH (US)

( * ) Notice: Subject to any disclaimer, the term of this patent is extended or adjusted under 35 U.S.C. 154(b) by 963 days.

(21) Appl. No.: 11/367,227

(22) Filed: Mar. 3, 2006

(65) Prior Publication Data

US 2006/0224237 A1    Oct. 5, 2006

Related U.S. Application Data

(60) Provisional application No. 60/658,385, filed on Mar. 3, 2005.

(51) Int. Cl.
*A61F 2/06* (2006.01)

(52) U.S. Cl. .................................... 623/1.46; 623/1.42

(58) Field of Classification Search ........................ None
See application file for complete search history.

(56) References Cited

U.S. PATENT DOCUMENTS

| | | | |
|---|---|---|---|
| 3,964,482 A | 6/1976 | Gerstel |
| 5,024,671 A | 6/1991 | Tu et al. |
| 5,051,272 A | 9/1991 | Hermes et al. |
| 5,067,491 A | 11/1991 | Taylor, II et al. |
| 5,073,381 A | 12/1991 | Ivan et al. |
| 5,102,417 A | 4/1992 | Palmaz |
| 5,108,424 A | 4/1992 | Hoffman, Jr. et al. |
| 5,185,408 A | 2/1993 | Tang et al. |
| 5,195,984 A | 3/1993 | Schatz |
| 5,197,977 A | 3/1993 | Hoffman, Jr. et al. |
| 5,246,452 A | 9/1993 | Sinnott |
| 5,263,349 A | 11/1993 | Felix et al. |
| 5,304,121 A | 4/1994 | Sahatjian |
| 5,316,023 A | 5/1994 | Palmaz |
| 5,383,928 A | 1/1995 | Scott et al. |
| 5,437,744 A | 8/1995 | Carlen |
| 5,449,382 A | 9/1995 | Dayton |
| 5,464,650 A | 11/1995 | Berg et al. |
| 5,500,013 A | 3/1996 | Buscemi et al. |
| 5,509,166 A | 4/1996 | Wagner et al. |
| 5,516,781 A | 5/1996 | Morris et al. |
| 5,545,208 A | 8/1996 | Wolff et al. |
| 5,556,754 A | 9/1996 | Singer |
| 5,563,146 A | 10/1996 | Morris et al. |
| 5,571,170 A | 11/1996 | Palmaz |
| 5,578,075 A | 11/1996 | Dayton |
| 5,578,645 A | 11/1996 | Askanazi |
| 5,605,696 A | 2/1997 | Eury |
| 5,616,608 A | 4/1997 | Kinsella et al. |
| 5,624,411 A | 4/1997 | Tuch |
| 5,632,840 A | 5/1997 | Campbell |
| 5,649,977 A | 7/1997 | Campbell |
| 5,665,728 A | 9/1997 | Morris et al. |
| 5,679,400 A | 10/1997 | Tuch |
| 5,695,516 A | 12/1997 | Fischell et al. |
| 5,716,981 A | 2/1998 | Hunter et al. |
| 5,725,572 A | 3/1998 | Lam et al. |
| 5,733,925 A | 3/1998 | Kunz et al. |
| 5,735,871 A | 4/1998 | Sgro |
| 5,755,781 A | 5/1998 | Jayaraman |
| 5,772,864 A | 6/1998 | Møller et al. |
| 5,824,045 A | 10/1998 | Alt |
| 5,824,049 A | 10/1998 | Ragheb et al. |
| 5,843,172 A | 12/1998 | Yan |
| 5,849,368 A | 12/1998 | Hostettler et al. |
| 5,853,419 A | 12/1998 | Imran |
| 5,861,027 A | 1/1999 | Trapp |
| 5,879,370 A | 3/1999 | Fischell et al. |
| 5,911,732 A | 6/1999 | Hojeibane |
| 5,916,585 A | 6/1999 | Cook |
| 5,962,620 A | 10/1999 | Reich et al. |
| 5,964,798 A | 10/1999 | Imran |
| 5,968,091 A | 10/1999 | Pinchuk et al. |
| 5,981,568 A | 11/1999 | Kunz et al. |
| 5,993,972 A | 11/1999 | Reich et al. |
| 6,007,573 A | 12/1999 | Wallace et al. |
| 6,059,810 A | 5/2000 | Brown et al. |
| 6,066,325 A | 5/2000 | Wallace |
| 6,093,520 A | 7/2000 | Vladimirsky |
| 6,099,561 A | 8/2000 | Alt |
| 6,120,536 A | 9/2000 | Ding et al. |
| 6,146,358 A | 11/2000 | Rowe |
| 6,156,062 A | 12/2000 | McGuinness |
| 6,200,337 B1 | 3/2001 | Moriuchi et al. |
| 6,200,589 B1 | 3/2001 | Kennedy et al. |
| 6,200,960 B1 | 3/2001 | Khachigan |
| 6,206,916 B1 | 3/2001 | Furst |

(Continued)

FOREIGN PATENT DOCUMENTS

CA    2172187    6/2001

(Continued)

OTHER PUBLICATIONS

Matsuda, 2002. Device-directed therapeutic drug delivery systems. Journal of Controlled Release, vol. 78:125-131.*
Regar et al, 2001. Stent development and local drug delivery. British Medical Bulletin, vol. 59:277-248.*
Regar et al, 2001. Stent development and local drug delivery. British Medical Bulletin, vol. 59:277-248 (provided in the Mar. 18, 2009 office action).*
Matsuda, 2002. Device-directed therapeutic drug delivery systems. Journal of Controlled Release, vol. 78:125-131 (provided in the Mar. 18, 2009 office action).*
*Trapidil Inhibits Monocyte Chemoattractant Protein-1 and macrophage Accumulation After Balloon Arterial Injury in Rabbits*, Poon M, Cohen J, Siddiqui Z, et al., Lab Invest 1999; 79:1369-1375.
*The TRAPIST study—A multicentre randomized placebo controlled clinical trial of trapidil for prevention of restenosis after coronary stenting, measured by 3-D intravascular ultrasound*, P.W. Serruys, D.P. Foley, M. Pieper, J.A. de Feyter on behalf of the TRAPIST investigators, European Heart Journal (2001) 22, 1938-1947, doi:10.1053/euhj.2001.2627, available online at http://www.idealibrary.com.

(Continued)

Primary Examiner — Suzanne Ziska
(74) Attorney, Agent, or Firm — Fay Sharpe LLP; Brian E. Turung

(57) ABSTRACT

A medical device that includes at least one surface structure and/or micro-structure that is at least partially coated with a protective coating.

44 Claims, 4 Drawing Sheets

U.S. PATENT DOCUMENTS

| | | | |
|---|---|---|---|
| 6,221,099 B1 | 4/2001 | Andersen et al. | |
| 6,240,616 B1 | 6/2001 | Yan | |
| 6,258,121 B1 | 7/2001 | Yang et al. | |
| 6,299,604 B1 | 10/2001 | Ragheb et al. | |
| 6,334,856 B1* | 1/2002 | Allen et al. | 604/191 |
| 6,335,029 B1 | 1/2002 | Kamath et al. | |
| 6,358,556 B1 | 3/2002 | Ding et al. | |
| 6,365,171 B1 | 4/2002 | Kennedy et al. | |
| 6,365,616 B1 | 4/2002 | Kohn | |
| 6,368,658 B1 | 4/2002 | Schwarz et al. | |
| 6,391,052 B2 | 5/2002 | Buirge et al. | |
| 6,399,144 B2 | 6/2002 | Dinh et al. | |
| 6,419,692 B1 | 7/2002 | Yang et al. | |
| 6,436,133 B1 | 8/2002 | Furst et al. | |
| 6,517,571 B1 | 2/2003 | Brauker et al. | |
| 6,528,584 B2 | 3/2003 | Kennedy et al. | |
| 6,533,949 B1 | 3/2003 | Yeshurun | |
| 6,555,619 B1 | 4/2003 | Kennedy et al. | |
| 6,558,361 B1 | 5/2003 | Yeshurun | |
| 6,583,251 B1 | 6/2003 | Chaikof et al. | |
| 6,641,611 B2 | 11/2003 | Jayaraman | |
| 6,695,833 B1 | 2/2004 | Frantzen | |
| 6,726,923 B2 | 4/2004 | Lyer et al. | |
| 6,743,211 B1* | 6/2004 | Prausnitz et al. | 604/239 |
| 6,790,372 B2 | 9/2004 | Roy | |
| 6,814,049 B2 | 11/2004 | Vogel et al. | |
| 6,861,406 B2 | 3/2005 | Mascarenhas | |
| 6,887,851 B2 | 5/2005 | Mascarenhas | |
| 6,924,087 B2 | 8/2005 | Yeshurun | |
| 2001/0013166 A1 | 8/2001 | Yan | |
| 2001/0014717 A1 | 8/2001 | Hossainy et al. | |
| 2002/0032414 A1 | 3/2002 | Ragheb et al. | |
| 2002/0051730 A1 | 5/2002 | Bodnar et al. | |
| 2002/0054900 A1 | 5/2002 | Kamath et al. | |
| 2002/0082679 A1 | 6/2002 | Sirhan et al. | |
| 2002/0095133 A1 | 7/2002 | Gillis et al. | |
| 2002/0098278 A1 | 7/2002 | Bates | |
| 2002/0142974 A1 | 10/2002 | Kohn | |
| 2002/0155737 A1 | 10/2002 | Roy | |
| 2003/0026840 A1 | 2/2003 | Plank et al. | |
| 2003/0040790 A1 | 2/2003 | Furst | |
| 2003/0064098 A1 | 4/2003 | Kararliet al. | |
| 2003/0083646 A1 | 5/2003 | Sirhan et al. | |
| 2003/0093141 A1 | 5/2003 | DiMatteo et al. | |
| 2003/0099712 A1 | 5/2003 | Jayaraman | |
| 2003/0100499 A1 | 5/2003 | Epstein | |
| 2003/0199969 A1 | 10/2003 | Steinke et al. | |
| 2003/0216534 A1 | 11/2003 | Chaikof et al. | |
| 2003/0228364 A1 | 12/2003 | Nathan | |
| 2003/0229390 A1 | 12/2003 | Ashton | |
| 2003/0229392 A1 | 12/2003 | Wong | |
| 2003/0229393 A1 | 12/2003 | Kutryk et al. | |
| 2004/0072105 A1 | 4/2004 | Yeshurun | |
| 2004/0093076 A1 | 5/2004 | White | |
| 2004/0093077 A1 | 5/2004 | White | |
| 2004/0098014 A1 | 5/2004 | Flugelman | |
| 2005/0029223 A1 | 2/2005 | Yeshurun | |
| 2005/0165358 A1 | 7/2005 | Yeshurun | |
| 2005/0209566 A1 | 9/2005 | Yeshurun | |
| 2006/0051404 A1 | 3/2006 | Yeshurun | |
| 2008/0038307 A1* | 2/2008 | Hoffmann | 424/423 |

FOREIGN PATENT DOCUMENTS

| | | |
|---|---|---|
| EP | 734721 | 2/1996 |
| EP | 714640 | 6/1996 |
| EP | 756853 | 2/1997 |
| WO | WO 94/16706 | 8/1994 |
| WO | WO 94/26291 | 11/1994 |
| WO | WO 96/25176 | 8/1996 |
| WO | WO 97/10011 | 3/1997 |
| WO | WO 98/17331 | 4/1998 |
| WO | WO 98/43618 | 10/1998 |
| WO | WO 99/18998 | 4/1999 |
| WO | WO 99/49907 | 10/1999 |
| WO | WO 99/56663 | 11/1999 |
| WO | WO 00/12175 | 3/2000 |
| WO | WO 01/01957 | 1/2001 |
| WO | WO 01/17577 | 3/2001 |
| WO | WO 01/17577 A1 | 3/2001 |
| WO | WO 01/41678 | 6/2001 |
| WO | WO 01/45763 | 6/2001 |
| WO | WO 01/97964 | 12/2001 |

OTHER PUBLICATIONS

Abstract of *Fast and Reproducible Vascular Neointima Formation in the Hamster Carotid Artery: Effects of Trapidil and Captopril*, Matsuno H, Stassen JM, Hoylaerts MF, Vermylen J, Deckmyn H., Thromb Haemost. Dec. 1995;74(6):1591-6.

*Results of a Meta-Analysis of Trapidil, a PDGF Inhibitor A' A Sufficient Reason for a Second Look to the Pharmacological Approach to Restenosis*, Serruys PW, Banz K, Darcis T, Mignot A, van Es GA, Schwicker D., J Invasive Cardiol. Oct. 1997;9(8):505-512.

*-New Aspects in Antithrombotic Therapy—Platelet Inhibitors-*, Terres W, Meinertz T., Herz. Feb. 1996;21(1):1-11.

*A Randomized Comparison of Trapidil (triazolopyrimidine), a Platelet-Derived Growth Factor Antagonist, Versus Aspirin in Prevention of Angiographic Restenosis after Coronary Artery Palmaz-Schatz Stent Implantation*, Galassi AR, Tamburino C, Nicosia A, Russo G, Grassi R, Monaco A, Giuffrida G., Catheter Cardiovasc Interv. Feb. 1999;46(2):162-8.

*Reference Chart Derived From Post-Stent-Implantation Intravascular Ultrasound Predictors of 6-Month Expected Restenosis on Quantitative Coronary Angiography*, P. J. de Feyter, P. Kay, C. Disco, and P. W. Serruys, Circulation, Oct. 1999; 100: 1777-1783.

Abstract of *Trapidil in Preventing Restenosis After Balloon Angioplasty in the Ather Osclerotic Rabbit*, MW Liu, GS Roubin, KA Robinson, AJ Black, JA Hearn, RJ Siegel, and SB King, 3d Circulation 1990 81: 1089-1093.

Abstract of *Effects of Trapidil (Triazolopyrimidine), a Platelet-Derived Growth Factor Antagonist, in Preventing Restenosis After Percutaneous Transluminal Coronary Angioplasty*, Okamoto S, Inden M, Setsuda M, Konishi T, Nakano T, Am Heart J. Jun. 1992; 123(6):1439-44.

Abstract of *Trapidil (triazolopyrimidine), A Platelet-Derived Growth Factor Antagonist, Reduces Restenosis After Percutaneous Transluminal Coronary Angioplasty. Results of the Randomized, Double-Blind STARC Study. Studio Trapidil Versus Aspirin Nella Restenosi Coronarica*, A Maresta, M Balducelli, L Cantini, A Casari, R Chioin, M Fabbri, A Fontanelli, PA Monici Preti, S Repetto, and S De Serv, Circulation, Dec. 1994; 90: 2710-2715.

Abstract of *The Trapidil Restenosis Trial (STARC study): Background, Methods and Clinical Characteristics of the Patient Population*, Maresta A, Balducelli M, Cantini L, Casari A, Chioin R, Fontanelli A, Monici Preti PA, Repetto S, Raffaghello S.,Clin Trials Metaanal. Apr. 1994;29(1):31-40.

Abstract of *Pharmacological Properties of Trapidil: Comparison with Other Coronary Vasodilators*, Ohnishi H, Kosuzume H, Yamaguchi K, Sato M, Umehara S, Funato H, Itoh C, Suzuki K, Kitamura Y, Suzuki Y, Itoh R., Nippon Yakurigaku Zasshi. Sep. 1980; 76(6):495-503.

Abstract of *Effects of Trapidil on Thromboxane A2-induced Aggregation of Platelets, Ischemic Changes in Heart and Biosynthesis of Thromboxane A2*, Ohnishi H, Kosuzume H, Hayashi Y, Yamaguchi K, Suzuki Y, Itoh R., Prostaglandins Med. Mar. 1981;6(3):269-81.

Abstract of *Antithrombotic Activity and the Mechanism of Action of Trapidil (Rocornal)*, Suzuki Y, Yamaguchi K, Shimada S, Kitamura Y, Ohnishi H., Prostaglandins Leukot Med. Dec. 1982;9(6):685-95.

Abstract of *Suppression of Fibroblast Proliferation In Vitro and of Myointimal Hyperplasia In Vivo by the Triazolopyrimidine, Trapidil*, Tiell ML, Sussman IL, Gordon PB, Saunders RN, Artery. 1983;12(1):33-50.

Trapidil in Preventing Restenosis After Balloon Angioplasty in the Atherosclerotic Rabbit, Liu, et al., *Circulation*, vol. 81, No. 3, Mar. 1990.

*Progress in Cardiovascular Disease*, Sonnenblick, et al., Sep./Oct. 1996.

*USCI PE Plus Peripheral Balloon Dilatation Catheter* brochure.

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

*Influence of Cardiovascular Drugs on Platelet Aggregation*, Forster W, Block HU, Giessler C, Heinroth I, Mentz P, Ponicke K, Rettkowski W, Zehl U., : Adv Myocardiol. 1983;4:539-47.

*Management of restenosis after Coronary Intervention*, Dangas G, Fuster, V., Am Heart J. Aug. 1996;132(2 Pt 1):428-36.

DNA Delivery from Polymer Matrices for Tissue Engineering, Shea, et al., *Nature Biotechnology*, vol. 17, Jun. 1999.

Polymeric System for Dual Growth Factor Delivery, Richardson, et al., *Nature Biotechnology*, vol. 19, Nov. 2001.

Controlled Growth Factor Release from Synthetic Extracellular Matrices, Lee, et al., *Nature*, vol. 408, Dec. 21/28, 2000.

Metals handbook Desk Edition, $2^{nd}$ Edition. Copyright 1998 by ASM Intl.

* cited by examiner

FRAGILE STRUCTURE PROTECTIVE COATING

The present invention claims priority on U.S. Provisional Application Ser. No. 60/658,385 filed Mar. 3, 2005, entitled "FRAGILE STRUCTURE PROTECTIVE COATING", which is incorporated herein.

The invention relates generally to medical devices, and more particularly to an implant for use within a body and, even more particularly to an expandable graft which is particularly useful for repairing various types of body passageways, and still even more particularly to an expandable graft that at least partially includes one or more surface structures and/or micro-structures.

BACKGROUND OF THE INVENTION

Medical treatment of various illnesses or diseases commonly include the use of one or more medical devices. Two types of medical devices that are commonly used to repair various types of body passageways are an expandable graft or stent, or a surgical graft. These devices have been implanted in various areas of the mammalian anatomy.

Old age, dietary habits and primary genetics can also lead to a common disease, atherosclerosis. Atherosclerotic plaques and blockages consist of lipids, fibroblasts and fibrin that proliferate and cause obstruction of a vessel. As the obstruction grows, the blood flow diminishes and reaches a level that is insufficient to meet the biological needs of one or more organs. The end result is defined as ischemia.

One purpose of a stent is to open a blocked or partially blocked body passageway. When a stent is used in a blood vessel, the stent is used to open the occluded vessel to achieve improved blood flow which is necessary to provide for the anatomical function of an organ. The procedure of opening a blocked or partially blocked body passageway commonly includes the use of one or more stents in combination with other medical devices such as, but not limited to, an introducer sheath, a guiding catheter, a guide wire, an angioplasty balloon, etc.

Various physical attributes of a stent or graft can contribute directly to the success rate of the device. These physical attributes include radiopacity, hoop strength, radial force, thickness of the metal, dimensions of the metal and the like. Stainless steel, cobalt and chromium are commonly used to form stents. A few stents are also formed of plastics or fiberglass. These materials are commonly used since such materials having a known history of safety, effectiveness and biocompatibility.

ICON Medical Corp. has developed technology that formed one or more surface structures and/or micro-structures on a medical device to facilitate in the success and/or use of the medical device. Typically, these surface structures and/or micro-structures are small and fragile structures that can become damaged when the medical device is packaged, handled, conveyed to a treatment area, etc. When such structures are damaged, the medical device can become fully or partially impaired.

In view of the current state of the art with regard to surface structures and/or micro-structures on a medical device, ICON Medical Corp. has developed new technology to address the problems stated above with regard to such surface structures and/or micro-structures on a medical device.

SUMMARY OF THE INVENTION

The medical device of the present invention is a device designed to be implantable in and/or placed on one or more regions of a body of a patient. The medical device includes one or more surface structures or micro-surface structures that are used to facilitate in the operation, function and/or success of the medical device. The medical device of the present invention also includes one or more coatings of protective material that are used to protect the surface structures and/or micro-surface structures on the medical device from damage. Typically, these surface structures and/or micro-surface structures are small fragile structures, and/or are formed of one or more materials that can be easily damaged. The one or more coatings of protective material that are used to cover the surface structures and/or micro-surface structures on the medical device can also or alternatively be used to at least partially shield the surface structures and/or micro-surface structures from an exterior environment. The surface structures and/or micro-surface structures can be formed of one or more materials that can at least partially dissolve, degrade and/or be absorbed in certain environmental conditions (e.g., exposure to fluids in a body passageway, exposure to enzymes in a body passageway, exposure to air, etc.). In one non-limiting embodiment of the invention, the one or more coatings of protective material are designed and/or formulated to at least partially shield or protect these one or more micro-structures and/or surface structures such as, but not limited to, when the medical device is 1) packaged and/or stored, 2) unpacked, 3) connected to and/or otherwise secured and/or placed on another medical device, 4) inserted into a treatment area, 5) handled by a user, 6) form a barrier between one or more micro-structures and/or surface structures and fluids in the body passageway, and/or form a barrier between one or more micro-structures and/or surface structures and air and/or other gasses in the atmosphere and/or in the body passageway. As can be appreciated, the one or more coatings of protective material can be designed and/or formulated to at least partially shield and/or protect these one or more micro-structures and/or surface structures in other and/or alternative situations. In another and/or alternative non-limiting embodiment of the invention, the one or more coatings of protective material can be designed and/or formulated to at least partially control 1) the rate of exposure of the one or more micro-structures and/or surface structures to a particular environment (e.g., fluids in a body passageway, gasses in the lungs, bile in a bile duct, air in the surrounding atmosphere, etc.), 2) the rate at which one or more micro-structures and/or surface structures degrades, dissolves and/or is absorbed, and/or 3) the rate at which one or more biological agents are released from the one or more micro-structures and/or surface structures. As can be appreciated, the one or more coatings of protective material can be designed and/or formulated to control the rate or other or additional aspects of the one or more micro-structures and/or surface structures on the medical device. In still another and/or alternative non-limiting embodiment of the invention, the one or more coatings of protective material can be designed and/or formulated to facilitate in the use of the one or more micro-structures and/or surface structures such as, but not limited to, 1) providing a smooth coating surface on at least a portion of the one or more micro-structures and/or surface structures, 2) providing a rough coating surface on at least a portion of the one or more micro-structures and/or surface structures, and/or 3) facilitating in one or more of the micro-structures and/or surface structures to at least partially secure to, engage with and/or penetrate into a body portion. As can be appreciated, the one or more coatings of protective material can be designed and/or formulated to have other and/or additional functions.

In another and/or alternative non-limiting aspect of the invention, the one or more coatings of protective material can be formed of a variety of materials (e.g., metals, polymers, biological agents, adhesives, sugars [e.g., glucose, fructose, sucrose, etc.], carbohydrate compounds, paraffins, starches, salts [e.g., NaCl, etc.], etc.). The one or more materials that form the one or more coatings of protective material can be porous, non-porous, biostable, biodegradable (i.e., dissolves, degrades, is absorbed, or any combination thereof in the body), and/or biocompatible. When one or more polymers are used to at least partially or fully make up the one or more coatings of protective material, the one or more polymers can be porous, non-porous, biostable, biodegradable (i.e., dissolves, degrades, is absorbed, or any combination thereof in the body), and/or biocompatible. When one or more coating layers of polymer are used to at least partially or fully make up the one or more coatings of protective material, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers can be polymers that are considered to be biodegradable, bioresorbable, or bioerodable; polymers that are considered to be biostable; and/or polymers that can be made to be biodegradable and/or bioresorbable with modification. Non-limiting examples of polymers that are considered to be biodegradable, bioresorbable, or bioerodable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g., DL-PLA), with and without additives (e.g., calcium phosphate glass), and/or other copolymers (e.g., poly(caprolactone lactide), poly(lactide glycolide), poly(lactic acid ethylene glycol)); poly(ethylene glycol); poly(ethylene glycol)diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA idextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. Non-limiting examples of polymers that considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g., polystyrene); poly(vinyl ethers) (e.g., polyvinyl methyl ether); poly(vinyl ketones); poly(vinylidene halides) (e.g., polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g., polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g., polyvinyl acetate); and/or copolymers, blends, and/or composites of above. Non-limiting examples of polymers that can be made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used to at least partially for the one or more protective coatings of protective material. In one non-limiting embodiment, the one or more polymers used to partially or fully make up the one or more coatings of protective material can include parylene, PLGA, POE, PGA, PLLA, PAA, PEG, chitosan and/or derivatives of one or more of these polymers.

In still another and/or alternative non-limiting aspect of the invention, the one or more coatings of protective material can include and/or be coated with one or more biological agents. The term "biological agent" includes, but is not limited to, a substance, drug, or otherwise formulated and/or designed to prevent, inhibit and/or treat one or more biological problems, and/or to promote the healing in a treated area. Non-limiting examples of biological problems that can be addressed by one or more biological agents include, but are not limited to, viral, fungus and/or bacteria infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; and/or the like. Non-limiting examples of biological agents that can be used include, but are not limited to, 5-Fluorouracil and/or derivatives thereof; 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca_{2+}$ transport such as L-type (e.g., diltiazem, nifedipine, verapamil, etc.) or T-type $Ca_{2+}$ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; anti-biotics; anti-coagulant compounds and/or derivatives thereof; anti-fibrosis compounds and/or derivatives thereof; anti-fungal compounds and/or derivatives thereof; anti-inflammatory compounds and/or derivatives thereof; Anti-Invasive Factor and/or derivatives thereof; anti-metabolite compounds and/or derivatives thereof (e.g., staurosporin, trichothecenes, and modified diphtheria and ricin toxins, Pseudomonas exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca_{2+}$/calmodulin kinase II, casein kinase II, etc.); aspirin and/or derivatives thereof; azathioprine and/or derivatives thereof; β-Estradiol and/or derivatives thereof; β-1-anticollagenase and/or derivatives thereof; calcium channel blockers and/or derivatives thereof; calmodulin antagonists and/or derivatives thereof (e.g., $H_7$, etc.); CAPTOPRIL and/or derivatives thereof; cartilage-derived inhibitor and/or derivatives thereof; ChIMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and/or derivatives thereof; endothelin and/or derivatives thereof; endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein IIb/IIIa platelet membrane receptor antibody and/or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the $IP_3$ receptor and/or derivatives thereof; inhibitors of the sodium/hydrogen antiporter and/or derivatives thereof (e.g., amiloride and derivatives thereof, etc.); insulin and/or derivatives thereof; Interferon alpha 2 Macroglobulin and/or derivatives thereof; ketoconazole and/or derivatives thereof; Lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; Plasminogen Activator Inhibitor-I and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, $H_3P^{32}O_4$, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; THI and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anti-coagulant peptide and/or derivatives thereof; thioprotese inhibitors and/or derivatives thereof; thyroid hormone and/or derivatives thereof; Tissue Inhibitor of Metalloproteinase-1 and/or derivatives thereof; Tissue Inhibitor of Metalloproteinase-2 and/or derivatives thereof; tissue plasma activators; TNF and/or derivatives thereof, tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the biological agent can include one or more derivatives of the above listed compounds and/or other compounds. In one non-limiting embodiment, the biological agent includes, but is not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The type and/or amount of biological agent included on, in, and/or in conjunction with the one or more coatings of protective material is generally selected for the treatment of one or more medical treatments. Typically, the amount of biological agent included on, in and/or used in conjunction with the one or more coatings of protective material is about 0.01-100 ug per $mm^2$; however, other amounts can be used. The amount of two or more biological agents on, in, and/or used in conjunction with the medical device can be the same or different. The one or more biological agents can be coated on and/or impregnated in the one or more coatings of protective material by a variety of mechanisms such as, but not limited to, spraying (e.g., atomizing spray techniques, etc.), dip coating, roll coating, sonication, brushing, plasma deposition, depositing by vapor deposition.

In still another and/or alternative non-limiting aspect of the invention, the one or more coatings of protective material can fully or partially cover and/or coat the one or more of the micro-structures and/or surface structures on the medical device. In one non-limiting embodiment of the invention, the one or more coatings of protective material that at least partially forms a coating layer generally follow the profile of the one or more of the micro-structures and/or surface structures on the medical device; however, this is not required. In one non-limiting aspect of this embodiment, the coating thickness of such a coating is generally at least about 0.001 µm and typically less than about 500 µm; however, other thicknesses can be used depending on the size and/or shape of the one or more of the micro-structures and/or surface structures on the medical device. In another and/or alternative aspect of this embodiment, the thickness of the one or more coatings of protective material form a coating layer that is about 0.01-150 µm, and typically about 0.1-50 µm; however, it will be appreciated that other thicknesses can be used. In another and/or alternative embodiment of the invention, the one or more coatings of protective material form a coating layer that partially or fully embeds one or more of the micro-structures and/or surface structures on the medical device within the one or more coatings of protective material. The coating thickness of such a coating typically depends on the size and/or shape of the one or more of the micro-structures, and/or surface structures on the medical device, and/or whether the one or more coatings of protective material are to be partially or fully embedded within the one or more coatings of protective material.

In yet another and/or alternative non-limiting aspect of the invention, medical devices that can include the one or more micro-structures, internal structures and/or surface structures and the one or more coatings of protective material include, but are not limited to, stents, grafts, vascular grafts, valves, orthopedic implants, sheaths, guide wires, an orthopedic device, PFO (patent foramen ovale) device, other types of grafts, guide catheter, stent catheters, electrophysiology catheters, other type of implant, a suture, staple, surgical graft, bandage, wrap, balloon catheters, hypotubes, catheters, cutting devices, etc. In one non-limiting embodiment of the invention, the medical device is directed for use in a body passageway. As defined herein, the term "body passageway" is defined herein to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). For vascular applications, the term "body passageway" primarily refers to blood vessels and chambers in the heart. When the medical device is in the form of a stent, the stent can be an expandable stent that is expandable by a balloon and/or other means. An expandable stent can be deployed at the same time an angioplasty procedure is performed; however, this is not required. The medical device can be at least partially 1) a biodegradable device that at least partially dissolves in the body and/or is absorbed by the body and/or 2) a biostable device that resists or does not dissolve in the body and/or is absorbed by the body. The medical device is typically made of a material that imparts the desirable mechanical properties to the medical device (e.g., strength, durability, hardness, biostability, bendability, coefficient of friction, radial strength, flexibility, tensile strength, tensile elongation, longitudinal lengthening, stress-strain properties, improved recoil properties, radiopacity, heat sensitivity, biocompatibility, etc.). The material used to form the medical device is also typically selected to withstand the manufacturing process that is needed to be accomplished in order to produce the medical device. These manufacturing processes can include, but are not limited to, laser cutting, etching, crimping, annealing, drawing, pilgering, electroplating, electro-polishing, chemical polishing, cleaning, pickling, ion beam deposition or implantation, sputter coating, vacuum deposition, MEMS (e.g., micro-machining, etc.) processes, ion beam deposition or implantation, and/or other processes. When the medical device is in the form of a stent, the stent is designed to be insertable in a treatment area in a body passageway and expand/stabilize the treatment area. The stent can include one or more biological agents that can inhibit thrombosis, in-stent restenosis, vascular narrowing and/or restenosis after the stent has been inserted into the blood vessel; however, the biological agents can have other and/or additional functions (e.g., reduce pain, reduce infection, remove and/or dissolve lipids, fibroblast, fibrin, etc. from the blood vessel, etc.).

In still yet another and/or alternative non-limiting aspect of the present invention, a variety of polymers can be coated on and/or at least partially form the medical device. The one or more polymers can be porous, non-porous, biostable, biodegradable (i.e., dissolves, degrades, is absorbed, or any combination thereof in the body), and/or biocompatible. When one or more coating layers of polymer are applied to the medical device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. A non-limiting list of one or more polymers that can be coated on the medical device and/or at least partially form the medical device have been previously listed above with respect to the protective coating composition. In one non-limiting embodiment of the invention, when the medical device includes one or more polymer layers, the thickness of each polymer layer is generally at least about 0.01 µm. In one non-limiting aspect of this embodiment, the thickness of each polymer layer is generally less than about 150 µm; however, larger thicknesses can be used. In another and/or alternative non-limiting aspect of this embodiment, the thickness of each polymer layer is about 0.02-75 µm, more particularly about 0.05-50 µm, and even more particularly about 1-30 µm. As can be appreciated, other thicknesses can be used. In one non-limiting embodiment, the medical device includes and/or is coated with parylene, PLGA, POE, PGA, PLLA, PAA, PEG, chitosan and/or derivatives of one or more of these polymers. In another and/or alternative non-limiting embodiment, the medical device includes and/or is coated with a non-porous polymer that includes, but is not limited to, polyamide, parylene c, parylene n and/or a parylene derivative. In still another and/or alternative non-limiting embodiment, the medical device includes and/or is coated with poly(ethylene oxide), poly(ethylene glycol), and poly(propylene oxide), polymers of silicone, methane, tetrafluoroethylene (including TEFLON brand polymers), tetramethyldisiloxane, and the like.

In still another and/or alternative non-limiting aspect of the present invention, a variety of metals can be coated on and/or at least partially form the medical device. The one or more metals that can at least partially form the medical device can include, but are not limited to, aluminum, barium, bismuth, calcium, cobalt, copper, chromium, gold, iron, stainless steel, titanium, vanadium, nickel, zirconium, niobium, lead, molybdenum, platinum, magnesium, yttrium, calcium, rare earth metals, rhenium, zinc, silver, depleted radioactive elements, tantalum, tungsten and/or alloys thereof (e.g., nitinol, etc.). As can be appreciated, other or additional metals can be used. The metal composition that forms one or more portions of the medical device can be at least partially biostable, bioabsorbable, etc.

In a further and/or alternative non-limiting aspect of the present invention, the medical device or one or more regions of the medical device can be constructed by use of one or more microelectromechanical manufacturing techniques (MEMS (e.g., micro-machining, laser micro-machining, laser micro-machining, micro-molding, etc.); however, other or additional manufacturing techniques can be used. The medical device can include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology. The medical device can include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the medical device. As defined herein, a micro-structure is a structure that has at least one dimension (e.g., average width, average diameter, average height, average length, average depth, etc.) that is no more than about 2 mm, and typically no more than about 1 mm. As can be appreciated, the medical device, when including one or more surface structures, a) all the surface structures can be micro-structures, b) all the surface structures can be non-micro-structures, or c) a portion of the surface structures can be micro-structures and a portion can be non-micro-structures. Non-limiting examples of structures that can be formed on the medical devices such as stents are illustrated in United States Patent Publication Nos. 2004/0093076 and 2004/0093077, which are incorporated herein by reference. Typically, the micro-structures, when formed, extend from or into the outer surface no more than about 400 microns, and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and/or be designed so as to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has been positioned on and/or in a patient; however, this is not required. The one or more surface structures and/or micro-structures can be used to facilitate in form-ing maintaining a shape of a medical device (i.e., see devices in United States Patent Publication Nos. 2004/0093076 and 2004/0093077). The one or more surface structures and/or micro-structures can be at least partially formed by MEMS (e.g., micro-machining, laser micro-machining, micro-molding, etc.) technology; however, this is not required. In one non-limiting embodiment, the one or more surface structures and/or micro-structures can be at least partially formed of a biological agent and/or be formed of a polymer. One or more of the surface structures and/or micro-structures can include one or more internal passageways that can include one or more materials (e.g., biological agent, polymer, etc.); however, this is not required. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the medical device can be used for a variety of purposes such as, but not limited to, 1) increasing the bonding and/or adhesion of one or more biological agents, adhesives, marker materials and/or polymers to the medical device, 2) changing the appearance or surface characteristics of the medical device, and/or 3) controlling the release rate of one or more biological agents. The one or more micro-structures and/or surface structures can be biostable, biodegradable, etc. One or more regions of the medical device that are at least partially formed by micro-electromechanical manufacturing techniques can be biostable, biodegradable, etc.

In still a further and/or alternative aspect of the present invention, the medical device can include one or more biological agents. A non-limiting list of one or more biological agents that can be coated on the medical device and/or at least partially form and/or included in the medical device have been previously listed above with respect to the protective coating composition. In addition, the amount of the one or more biological agents used on and/or included in the medical device can be similar to the amounts indicated above with respect to the protective coating composition. The one or more biological agents on and/or in the medical device, when used on the medical device, can be released in a controlled manner so the area in question to be treated is provided with the desired dosage of biological agent over a sustained period of time. As can be appreciated, controlled release of one or more biological agents on the medical device is not always required and/or desirable. As such, one or more of the biological agents on and/or in the medical device can be uncontrollably released from the medical device during and/or after insertion of the medical device in the treatment area. It can also be appreciated that one or more biological agents on and/or in the medical device can be controllably released from the medical device and one or more biological agents on and/or in the medical device can be uncontrollably released from the medical device. It can also be appreciated that one or more biological agents on and/or in one region of the medical device can be controllably released from the medical device and one or more biological agents on and/or in the medical device can be uncontrollably released from another region on the medical device. As such, the medical device can be designed such that 1) all the biological agent on and/or in the medical device is controllably released, 2) some of the biological agent on and/or in the medical device is controllably released and some of the biological agent on the medical device is non-controllably released, or 3) none of the biological agent on and/or in the medical device is controllably released. The medical device can also be designed such that the rate of release of the one or more biological agents from the medical device is the same or different. The medical device can also be designed such that the rate of release of the one or more biological agents from one or more regions on the medical device is the same or different. Non-limiting arrangements that can be used to control the release of one or more biological agent from the medical device include a) at least partially coat one or more biological agents with one or more polymers, b) at least partially incorporate and/or at least partially encapsulate one or more biological agents into and/or with one or more polymers, and/or c) insert one or more biological agents in pores, passageway, cavities, etc. in the medical device and at least partially coat or cover such pores, passageway, cavities, etc. with one or more polymers. As can be appreciated, other or additional arrangements can be used to control the release of one or more biological agent from the medical device. The one or more polymers used to at least partially control the release of one or more biological agent from the medical device can be porous or non-porous. The one or more biological agents can be inserted into and/or applied to one or more surface structures and/or micro-structures on the medical device, and/or be used to at least partially form one or more surface structures and/or micro-structures on the medical device. As such, the one or more biological agents on the medical device can be 1) coated on one or more surface regions of the medical device, 2) inserted and/or impregnated in one or more surface structures and/or micro-structures, etc. of the medical device, and/or 3) form at least a portion or be included in at least a portion of the structure of the medical device. When the one or more biological agents are coated on the medical device, the one or more biological agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. When the one or more biological agents are inserted and/or impregnated in one or more internal structures, surface structures and/or micro-structures of the medical device, 1) one or more other coating materials can be applied at least partially over the one or more internal structures, surface structures and/or micro-structures of the medical device, and/or 2) one or more polymers can be combined with one or more biological agents. As such, the one or more biological agents can be 1) embedded in the structure of the medical device; 2) positioned in one or more internal structures of the medical device; 3) encapsulated between two polymer coatings; 4) encapsulated between the base structure and a polymer coating and/or protective coating; 5) mixed in the base structure of the medical device that includes at least one polymer coating; or 6) one or more combinations of 1, 2, 3, 4 and/or 5. In addition or alternatively, the one or more coatings of the one or more polymers on the medical device can include 1) one or more coatings of non-porous polymers; 2) one or more coatings of a combination of one or more porous polymers and one or more non-porous polymers; 3) one or more coating of porous polymer, or 4) one or more combinations of options 1, 2, and 3. As can be appreciated different biological agents can be located in and/or between different polymer coating layers and/or on and/or the structure of the medical device. As can also be appreciated, many other and/or additional coating combinations and/or configurations can be used. The concentration of one or more biological agents, the type of polymer, the type of protective coating, the type and/or shape of internal structures in the medical device and/or the coating thickness of one or more biological agents can be used to control the release time, the release rate and/or the dosage amount of one or more biological agents; however, other or additional combinations can be used. As such, the biological agent and polymer system/protective coating combination and location on the medical device can be numerous. As can also be appreciated, one or more biological agents can be deposited on the top surface of the medical device to provide an initial uncontrolled burst effect of the one or more biological agents prior to 1) the controlled release of the one or more biological agents through one or more layers of polymer system/protective coating system and/or 2) the uncontrolled release of the one or more biological agents through one or more layers of polymer system/protective coating system. The one or more biological agents and/or polymers/protective coatings can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer and/or layer of biological agent is generally at least about 0.01 μm and is generally less than about 150 μm; however, thicker layers can be used. In one non-limiting embodiment, the thickness of a polymer layer and/or layer of biological agent is about 0.02-75 μm, more particularly about 0.05-50 μm, and even more particularly about 1-30 μm. When the medical device includes and/or is coated with one or more biological agents such that at least one of the biological agents is at least partially controllably released from the medical device, the need or use of body-wide therapy for extended periods of time can be reduced or eliminated. In the past, the use of body-wide therapy was used by the patient long after the patient left the hospital or other type of medical facility. This body-wide therapy could last days, weeks, months or sometimes over a year after surgery. The medical device of the present invention can be applied or inserted into a treatment area and 1) merely requires reduced use and/or extended use of body wide therapy after application or insertion of the medical device or 2) does not require use and/or extended use of body-wide therapy after application or insertion of the medical device. As can be appreciated, use and/or extended use of body wide therapy can be used after application or insertion of the medical device at the treatment area. In one non-limiting example, no body-wide therapy is needed after the insertion of the medical device into a patient. In another and/or alternative non-limiting example, short term use of body-wide therapy is needed or used after the insertion of the medical device into a patient. Such short term use can be terminated after the release of the patient from the hospital or other type of medical facility, or one to two days or weeks after the release of the patient from the hospital or other type of medical facility; however, it will be appreciated that other time periods of body-wide therapy can be used. As a result of the use of the medical device of the present invention, the use of body-wide therapy after a medical procedure involving the insertion of a medical device into a treatment area can be significantly reduced or eliminated. In another and/or alternative non-limiting embodiment of the invention, controlled release of one or more biological agents from the medical device, when controlled release is desired, can be accomplished by using one or more non-porous polymer layers/protective coatings; however, other and/or additional mechanisms can be used to controllably release the one or more biological agents. The one or more biological agents are at least partially controllably released by molecular diffusion through the one or more non-porous polymer/protective coating layers. When one or more non-porous polymer layers are used, the one or more polymer layers are typically biocompatible polymers; however, this is not required. The one or more non-porous polymers can be applied to the medical device without the use of chemical, solvents, and/or catalysts; however, this is not required. In one non-limiting example, the non-porous polymer can be at least partially applied by, but not limited to, vapor deposition and/or plasma deposition. The non-porous polymer can be selected so as to polymerize and cure merely upon condensation from the vapor phase; however, this is not required. The application of the one or more non-porous polymer layers can be accomplished without increasing the temperature above ambient temperature (e.g., 65-90° F.); however, this is not required. The non-porous polymer system can be mixed with one or more biological agents prior to being coated on the medical device and/or be coated on a medical device that previously included one or more biological agents; however, this is not required. The use of one or more non-porous polymer layers allow for accurate controlled release of the biological agent from the medical device. The controlled release of one or more biological agents through the non-porous polymer is at least partially controlled on a molecular level utilizing the motility of diffusion of the biological agent through the non-porous polymer. In one non-limiting example, the one or more non-porous polymer layers can include, but are not limited to, polyamide, parylene (e.g., parylene C, parylene N) and/or a parylene derivative. In still another and/or alternative non-limiting embodiment of the present invention, controlled release of one or more biological agents from the medical device, when controlled release is desired, can be accomplished by using one or more polymers/protective coatings that form a chemical bond with one or more biological agents. In one non-limiting example, at least one biological agent includes trapidil, trapidil derivative or a salt thereof that is covalently bonded to at least one polymer such as, but not limited to, an ethylene-acrylic acid copolymer. The ethylene is the hydrophobic group and acrylic acid is the hydrophilic group. The mole ratio of the ethylene to the acrylic acid in the copolymer can be used to control the hydrophobicity of the copolymer. The degree of hydrophobicity of one or more polymers can also be used to control the release rate of one or more biological agents from the one or more polymers. The amount of biological agent that can be loaded with one or more polymers may be a function of the concentration of anionic groups and/or cationic groups in the one or more polymer. For biological agents that are anionic, the concentration of biological agent that can be loaded on the one or more polymers is generally a function of the concentration of cationic groups (e.g., amine groups and the like) in the one or more polymer and the fraction of these cationic groups that can ionically bind to the anionic form of the one or more biological agents. For biological agents that are cationic (e.g., trapidil, etc.), the concentration of biological agents that can be loaded on the one or more polymers is generally a function of the concentration of anionic groups (i.e., carboxylate groups, phosphate groups, sulfate groups, and/or other organic anionic groups) in the one or more polymers, and the fraction of these anionic groups that can ionically bind to the cationic form of the one or more biological agents. As such, the concentration of one or more biological agents that can be bound to the one or more polymers can be varied by controlling the amount of hydrophobic and hydrophilic monomer in the one or more polymers, by controlling the efficiency of salt formation between the biological agent, and/or the anionic/cationic groups in the one or more polymers. In yet another and/or alternative non-limiting embodiment of the present invention, controlled release of one or more biological agents from the medical device, when controlled release is desired, can be accomplished by using one or more polymers/protective coatings that include one or more induced cross-links. These one or more cross-links can be used to at least partially control the rate of release of the one or more biological agents from the one or more polymers. The cross-linking in the one or more polymers can be instituted by a number to techniques such as, but not limited to, using catalysts, using radiation, using heat, and/or the like. The one or more cross-links formed in the one or more polymers can result in the one or more biological agents to become partially or fully entrapped within the cross-linking, and/or form a bond with the cross-linking. As such, the partially or fully biological agent takes longer to release itself from the cross-linking, thereby delaying the release rate of the one or more biological agents from the one or more polymers. Consequently, the amount of biological agent, and/or the rate at which the biological agent is released from the medical device over time can be at least partially controlled by the amount or degree of cross-linking in the one or more polymers.

In yet a further and/or alternative non-limiting aspect of the invention, the medical device can include a marker material that facilitates enabling the medical device to be properly positioned in a body passageway. The marker material is typically designed to be visible to electromagnetic waves (e.g., x-rays, microwaves, visible light, inferred waves, ultraviolet waves, etc.); sound waves (e.g., ultrasound waves, etc.); magnetic waves (e.g., MRI, etc.); and/or other types of electromagnetic waves (e.g., microwaves, visible light, inferred waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion; at ends of medical device; at or near transition of body portion and flaring section; etc.) of the medical device. The location of the marker material can be on one or multiple locations on the medical device. The size of the one or more regions that include the marker material can be the same or different. The marker material can be spaced at defined distances from one another so as to form ruler-like markings on the medical device to facilitate in the positioning of the medical device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. The metal which at least partially forms the medical device can function as a marker material; however, this is not required. When the marker material is a flexible material, the marker material typically is formed of one or more polymers that are marker materials in-of-themselves and/or include one or more metal powders and/or metal compounds. In one non-limiting embodiment, the flexible marker material includes one or more metal powders in combination with parylene, PLGA, POE, PGA, PLLA, PAA, PEG, chitosan and/or derivatives of one or more of these polymers. In another and/or alternative non-limiting embodiment, the flexible marker material includes one or more metals and/or metal powders of aluminum, barium, bismuth, cobalt, copper, chromium, gold, iron, stainless steel, titanium, vanadium, nickel, zirconium, niobium, lead, molybdenum, platinum, yttrium, calcium, rare earth metals, rhenium, zinc, silver, depleted radioactive elements, tantalum and/or tungsten; and/or compounds thereof. The marker material can be coated with a polymer protective material; however, this is not required. When the marker material is coated with a polymer protective material, the polymer coating can be used to 1) at least partially insulate the marker material from body fluids, 2) facilitate in retaining the marker material on the medical device, 3) at least partially shielding the marker material from damage during a medical procedure and/or 4) provide a desired surface profile on the medical device. As can be appreciated, the polymer coating can have other or additional uses. The polymer coating can be a biostable polymer or a biodegradable polymer (e.g., degrades and/or is absorbed). The coating thickness of the polymer material, when used, is typically less than about 300 microns; however, other thickness can be used. In one non-limiting embodiment, the polymer material includes parylene, PLGA, POE, PGA, PLLA, PAA, PEG, chitosan and/or derivatives of one or more of these polymers.

In still yet a further and/or alternative aspect of the invention, the medical device can be an expandable device that can be expanded by use of some other device (e.g., balloon, etc.) and/or is self expanding. The expandable medical device can be fabricated from a material that has no or substantially no shape memory characteristics or can be partially fabricated from a material having shape-memory characteristics. Typically, when one or more shape-memory materials are used, the shape memory material composition is selected such that the shape memory material remains in an unexpanded configuration at a cold temperature (e.g., below body temperature); however, this is not required. When the shape memory material is heated (e.g., to body temperature) the expandable body section can be designed to expand to at least partially seal and secure the stent in a body passageway or other region; however, this is not required.

In another and/or alternative non-limiting aspect of the present invention, the medical device can include and/or be used with a physical hindrance. The physical hindrance can include, but is not limited to, an adhesive, a sheath, a magnet, tape, wire, string, etc. The physical hindrance can be used to 1) physically retain one or more regions of the medical device in a particular form or profile, 2) physically retain the medical device on a particular deployment device, 3) protect one or more surface structures and/or micro-structures on the medical device, and/or 4) form a barrier between one or more surface regions, surface structures and/or micro-structures on the medical device and the fluids in a body passageway. As can be appreciated, the physical hindrance can have other and/or additional functions. The physical hindrance is typically a biodegradable material; however, a biostable material can be used. The physical hindrance can be designed to withstand sterilization of the medical device; however, this is not required. The physical hindrance can be applied to, included in and/or be used in conjunction with one or more medical devices. Additionally or alternatively, the physical hindrance can be designed to be used with and/or conjunction with a medical device for a limited period of time and then 1) disengage from the medical device after the medical device has been partially or fully deployed and/or 2) dissolve and/or degrade during and/or after the medical device has been partially or fully deployed; however, this is not required. Additionally, or alternatively, the physical hindrance can be designed and be formulated to be temporarily used with a medical device to facilitate in the deployment of the medical device; however, this is not required. In one non-limiting use of the physical hindrance, the physical hindrance is designed or formulated to at least partially secure a medical device to another device that is used to at least partially transport the medical device to a location for treatment. In another and/or alternative non-limiting use of the physical hindrance, the physical hindrance is designed or formulated to at least partially maintain the medical device in a particular shape or form until the medical device is at least partially positioned in a treatment location. In still another and/or alternative non-limiting use of the physical hindrance, the physical hindrance is designed or formulated to at least partially maintain and/or secure one type of medical device to another type of medical instrument or device until the medical device is at least partially positioned in a treatment location. The physical hindrance can also or alternatively be designed and formulated to be used with a medical device to facilitate in the use of the medical device. In one non-limiting use of the physical hindrance, when in the form of an adhesive, can be formulated to at least partially secure a medical device to a treatment area so as to facilitate in maintaining the medical device at the treatment area. For instance, the physical hindrance can be used in such use to facilitate in maintaining a medical device on or at a treatment area until the medical device is properly secured to the treatment area by sutures, stitches, screws, nails, rod, etc.; however, this is not required. Additionally or alternatively, the physical hindrance can be used to facilitate in maintaining a medical device on or at a treatment area until the medical device has partially or fully accomplished its objective. The physical hindrance is typically a biocompatible material so as to not cause unanticipated adverse effects when properly used. The physical hindrance can be biostable or biodegradable (e.g., degrades and/or is absorbed, etc.). When the physical hindrance includes or has one or more adhesives, the one or more adhesives can be applied to the medical device by, but is not limited to, spraying (e.g., atomizing spray techniques, etc.), dip coating, roll coating, sonication, brushing, plasma deposition, and/or depositing by vapor deposition, brushing, painting, etc.) on the medical device. The physical hindrance can also or alternatively form at least a part of the medical device. One or more regions and/or surfaces of a medical device can also or alternatively include the physical hindrance. The physical hindrance can include one or more biological agents and/or other materials (e.g., marker material, polymer, etc.); however, this is not required. When the physical hindrance is or includes an adhesive, the adhesive can be formulated to controllably release one or more biological agents in the adhesive and/or coated on and/or contained within the medical device; however, this is not required. The adhesive can also or alternatively control the release of one or more biological agents located on and/or contained in the medical device by forming a penetrable or non-penetrable barrier to such biological agents; however, this is not required. The adhesive can include and/or be mixed with one or more polymers; however, this is not required. The one or more polymers can be used to 1) control the time of adhesion provided by said adhesive, 2) control the rate of degradation of the adhesive, and/or 3) control the rate of release of one or more biological agents from the adhesive and/or diffusing or penetrating through the adhesive layer; however, this is not required. When the physical hindrance includes a sheath, the sheath can be designed to partially or fully encircle the medical device. The sheath can be designed to be physically removed from the medical device after the medical device is deployed to a treatment area; however, this is not required. The sheath can be formed of a biodegradable material that at least partially degrades over time to at least partially expose one or more surface regions, micro-structures and/or surface structures of the medical device; however, this is not required. The sheath can include and/or be at least partially coated with one or more biological agents. The sheath includes one or more polymers; however, this is not required. The one or more polymers can be used for a variety of reasons such as, but not limited to, 1) forming a portion of the sheath, 2) improving a physical property of the sheath (e.g., improve strength, improve durability, improve biocompatibility, reduce friction, etc.), and/or 3 at least partially controlling a release rate of one or more biological agents from the sheath. As can be appreciated, the one or more polymers can have other or additional uses on the sheath.

In still another and/or alternative non-limiting aspect of the invention, the medical device is in the form of a stent. The stent can be an expandable stent that is expandable by a balloon and/or is self-expanding. The stent can have one or more body members. The one or more body members can include first and second ends and a wall surface disposed between the first and second ends. Typically each body member has a first cross-sectional area which permits delivery of the body member into a body passageway, and a second, expanded cross-sectional area. The expansion of one or more body members of the stent can be accomplished in a variety of manners. In one manner, one or more body members are expanded to the second cross-sectional area by a radially, outwardly extending force applied at least partially from the interior region of the body member (e.g., by use of a balloon, etc.). The body member can include shape memory materials; however, this is not required. The second cross-sectional area of the stent can be fixed or variable. The stent can be designed such that one or more body members expand while substantially retaining the original longitudinal length of the body member; however, this is not required. The one or more body members can have a first cross-sectional shape that is generally circular so as to form a substantially tubular body member; however, the one or more body members can have other cross-sectional shapes. When the stent includes two or more body members, the two or more body members can be connected together by at least one connector member. The stent can include rounded, smooth and/or blunt surfaces to minimize and/or prevent potential damage to a body passageway as the stent is inserted into a body passageway and/or expanded in a body passageway; however, this is not required. The stent can be treated with gamma, beta and/or e-beam radiation, and/or otherwise sterilized; however, this is not required.

In yet another and/or alternative non-limiting aspect of the present invention, the medical device is designed to improve patient procedural outcome via implantation. The medical device is designed for the applicable system to be treated. The medical device can be designed to be used as a biological agent delivery mechanism to deliver one or more biological agents to and/or into a wall of a body passageway and/or downstream from the site of implantation of the medical device. In one non-limiting embodiment of the invention, the medical device is designed to deliver one or more biological agents directly into the wall of a body passageway. In another and/or alternative non-limiting embodiment of the invention, the medical device is designed to at least partially utilize molecular diffusion to deliver one or more biological agents to and/or into a wall of a body passageway and/or down stream from the site if implantation of the medical device; however, this is not required. When a molecular diffusion mechanism is used, this mechanism can be used to at least partially control the diffusion of one or more biological agents from the medical device. When a molecular diffusion mechanism is used on the medical device, one or more non-porous polymer layers can be used to facilitate in such molecular diffusion; however, this is not required. In still another and/or alternative non-limiting embodiment of the invention, the medical device is a biodegradable stent comprised of a biodegradable material that includes at least one layer of biological agent and at least one non-porous polymer layer applied at least partially over the layer of biological agent and/or surface of the stent so that the biological agent is at least partially controllably released from the medical device. In still yet another and/or alternative non-limiting embodiment of the invention, the medical device is a biostable stent comprised of a biostable metal alloy that includes at least one layer of biological agent and at least one non-porous polymer layer applied at least partially over the layer of biological agent and/or surface of the stent so that the biological agent is at least partially controllably released from the medical device. In another and/or alternative non-limiting embodiment of the invention, the medical device is a bioabsorbable stent comprised of a biodegradable metal alloy that includes at least one layer of biological agent and at least one non-porous polymer layer applied at least partially over the layer of biological agent and/or surface of the stent so that the biological agent is at least partially controllably released from the medical device. The molecular composition, molecular structure and/or coating thickness of the non-porous polymer can be selected to control the release rate of one or more biological agents from the medical device; however, this is not required.

In one non-limiting overview of the present invention, there is provided a medical device that is adapted for introduction into a patient. The medical device can be designed to include and/or to release one or more biological agents in a controlled and/or uncontrolled fashion; however, this is not required. For instance, all of the biological agent can be controllably released from the medical device, all of the biological agent can be uncontrollably released from the medical device, or some of the biological agent can be controllably released and some uncontrollably released from the medical device. Typically, the controlled release of the one or more biological agents is at least partially released by molecular diffusion through one or more non-porous polymer layers; however, it will be appreciated that other, or additional mechanism can be used to control the rate of release. The medical device can include one or more layers of polymer and/or biological agent on the surface structure of the medical device. The one or more polymers, when used, can include parylene, PLGA, POE, PGA, PLLA, PAA, PEG, chitosan and/or derivatives of one or more of these polymers; however, other or additional polymers can be used. Many different biological agents can be used on the medical device. Such biological agents include, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however, it will be appreciated that other or additional biological agents can be used. The polymer and/or biological agent that is included on and/or forms the medical device can be hydrophobic or hydrophilic, which can be used to facilitate in the controlled release of the one or more biological agents; however, this is not required. The thickness of the one or more polymer layers can be selected to facilitate in the controlled release of the one or more biological agents; however, this is not required. The molecular weight and/or molecular structure of the one or more biological agents and/or one or more polymers can be selected to facilitate in the release of the one or more biological agents; however, this is not required. The medical device can have a variety of applications such as, but not limited to placement into the vascular system, esophagus, trachea, colon, biliary tract, or urinary tract. As can be appreciated, the medical device can have other or additional uses. The structure of the medical device during manufacture can be pre-treated by plasma etching; however, this is not required. The medical device can include one or more layers of polymer and/or biological agent on the surface structure of the medical device; however, this is not required. At least one biological agent can be deposited underneath and/or combined with at least one non-porous polymer layer so as to control the release of the at least biological agent; however, this is not required. The medical device can also include one or more porous polymer; however, this is not required. One or more polymer layers can be applied by vapor deposition, plasma deposition, or another or additional coating technique. The non-porous polymer can include polyamide, parylene (e.g., parylene C, parylene N) and/or a parylene derivative; however, other or additional non-porous polymers can be used. When the medical device is in the form of a stent, the stent can be an expandable stent that is expanded by use of a balloon and/or is self expanding. The medical device can be in other forms such as, but not limited to, an orthopedic device, PFO (patent foramen ovale) device, other types of grafts, guide catheter, guide wide, sheaths, stent catheters, electrophysiology catheters, other type of implant, a suture, staple, surgical graft, bandage, wrap, biological glue, etc. The medical device can include one or more surface structures, micro-structures, internal structures that can include one or more biological agents, adhesives and/or polymers; however, this is not required. These structures can be at least partially formed by MEMS (e.g., micro-machining, etc.) technology and/or other types of technology. The structures can be designed to contain and/or a fluidly connected to a passageway that includes one or more biological agents; however, this is not required. The micro-structures can be designed to engage and/or penetrate surrounding tissue or organs once the medical device has been position on and/or in a patient; however, this is not required. One or more polymers, adhesive and/or biological agents can be inserted in these surface structures and/or at least partially form these surface structures of the medical device; however, this is not required. Typically, the micro-structures, when formed, extend from or into the outer surface no more than about 400 microns, and more typically, less than about 300 microns, and more typically about 15-250 microns; however, other sizes can be used. The micro-structures can be clustered together or disbursed throughout the surface of the medical device. The one or more surface and/or micro-structures are at least partially coated with one or more layers of protective material. The one or more coatings of protective material can be used to at least partially protect from damage one or more of these structures, at least partially control the rate such structures degrade, dissolve, absorb, etc., and/or at least partially control the release rate of one or more substances from such structures. As can be appreciated, the one or more coating of protective material can have other or additional functions. As can also be appreciated, the one or more coatings of protective materials can be formed of or include one or more biological agents. The one or more coatings of protective material can partially or fully embed one or more of the micro-structures. Similar shaped and/or sized micro-structures can be used, or different shaped and/or sized micro-structures can be used. The surface topography of the medical device can be uniform or vary to achieve the desired operation and/or biological agent released from the medical device. As can be appreciated, the medical device or one or more regions of the medical device can be constructed by use of one or more microelectromechanical manufacturing techniques (MEMS (e.g., micro-machining, etc.); however, this is not required. Materials that can be used by MEMS (e.g., micro-machining, etc.) technology include, but are not limited to, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, and/or a PEG derivative. The medical device is typically formed of a biocompatible material. The amount of biological agent, when used on the medical device, can be selected for different medical treatments. Typically, the amount of biological agent, when used, is about 0.01-100 ug per $mm^2$; however, other amounts can be used. As can be appreciated one or more biological agents and/or polymers can be placed on different regions of the medical device to achieve the desired operation and/or biological agent release from the medical device. The medical device can include one or more coatings of biological agent on the other surface of the medical device to provide a burst of biological agent to a particular site or region; however, this is not required. The one or more biological agents can be selected so as to be chemically bonded to one or more polymers; however, this is not required. The time period the one or more biological agents are released from the medical device can vary; however, this is not required. Generally, one or more biological agents are released from the medical device for at least several days after the medical device is inserted in the body of a patient; however, this is not required. One or more biological agents can be released from the medical device for at least about one week after the medical device is inserted in the body of a patient, more typically at least about two weeks after the medical device is inserted in the body of a patient, and even more typically, about one week to one year after the medical device is inserted in the body of a patient; however, this is not required. As can be appreciated, the time frame that one or more of the biological agents can be released from the medical device can be longer or shorter. One or more biological agents can be released from the medical device controllably and/or non-controllably released. The time period for the release of two or more biological agents from the medical device can be the same or different. The type of the one or more biological agents used on the medical device, the release rate of the one or more biological agents from the medical device, and/or the concentration of the one or more biological agents being released from the medical device during a certain time period is typically selected to deliver one or more biological agents directly to the area of disease after the medical device has been implanted; however, this is not required. The use of the medical device can be used in conjunction with other biological agents. For instance, the success of the medical device can be enhanced by infusing, injecting or consuming orally the same and/or different biological agent used for anti-platelet and/or anti-coagulation therapy that is being released controllably from the medical device. The introduction of biological agents from a source other than the medical device can have a synergistic effect which can enhance the success of the medical device. Solid dosage forms of biological agents for oral administration can be used. Such solid forms can include, but are not limited to, capsules, tablets, effervescent tablets, chewable tablets, pills, powders, sachets, granules and gels. In such solid dosage forms, the biological agent can be admixed with at least one filler material such as, but not limited to, sucrose, lactose or starch. Such dosage forms can also comprise, as in normal practice, additional substances such as, but not limited to, inert diluents (e.g., lubricating agents, etc.). When capsules, tablets, effervescent tablets or pills are used, the dosage form can also include buffering agents. Soft gelatin capsules can be prepared to contain a mixture of the biological agent in combination with vegetable oil or other types of oil. Hard gelatin capsules can contain granules of the biological agent in combination with a solid carrier such as, but not limited to, lactose, potato starch, corn starch, cellulose derivatives of gelatin, etc. Tablets and pills can be prepared with enteric coatings for additional time release characteristics. Liquid dosage forms of the biological agent for oral administration can include pharmaceutically acceptable emulsions, solutions, suspensions, syrups, elixirs, etc.

One non-limiting object of the present invention is the provision of a medical device that includes one or more surface structures or micro-structures that are at least partially coated with one or more coatings of protective material.

Another and/or alternative non-limiting object of the present invention is the provision of a medical device that is at least partially formed by MEMS (e.g., micro-machining, etc.) technology.

Still another and/or alternative non-limiting object of the present invention is the provision of a medical device that is coated and/or impregnated with one or more biological agents.

Yet another and/or alternative non-limiting object of the present invention is the provision of a medical device that includes one or more polymers to at least partially control the release rate of one or more biological agents.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
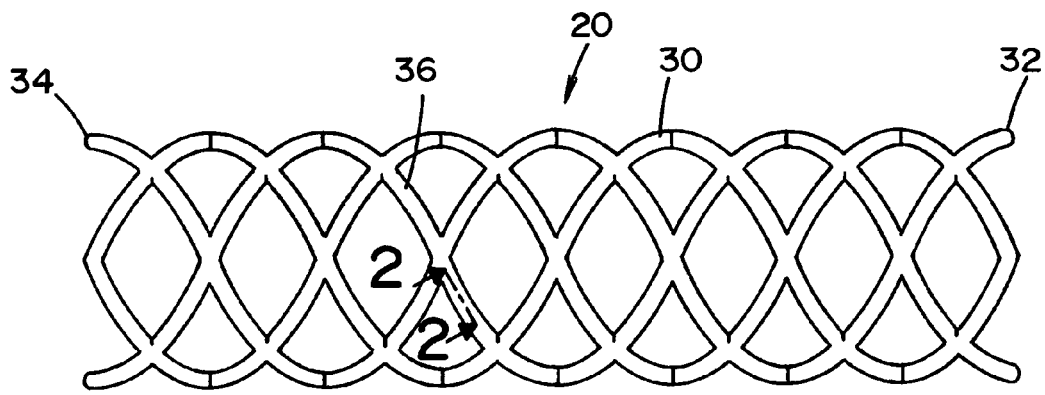
FIG. 1 is a perspective view of a section of an unexpanded stent which permits delivery of the stent into a body passageway.
Figure 2:
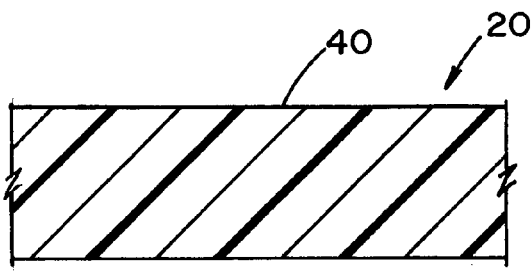
FIG. 2 is a cross-sectional view along line 2-2 of FIG. 1 illustrating a section that forms the stent.

Referring now to the drawings wherein the showings are for the purpose of illustrating the preferred embodiments only and not for the purpose of limiting the same, FIGS. 1-15 disclose a medical device in the form of a stent for use in a body passageway. The medical device of the present invention is designed to address the shortcomings of prior medical devices. The medical device includes one or more surface structures or micro-surface structures that are used to facilitate in the operation, function and/or success of the medical device. The medical device of the present invention also includes one or more coatings of protective material on one or more surface structures or micro-surface structures on the medical device. The one or more coatings of protective material can be used to protect these one or more micro-structures and/or surface structures from damage such as, but limited to, when the medical device is 1) packaged and/or stored, 2) unpacked, 3) connected to and/or other secured and/or placed on another medical device, 4) inserted into a treatment area, and/or 5) handled by a user. The one or more coatings of protective material can also or alternatively be used to form a barrier between one or more micro-structures and/or surface structures and fluids in the body passageway, and/or form a barrier between one or more micro-structures and/or surface structures and air and/or other gasses in the atmosphere and/or in the body passageway. The one or more coatings of protective material can also or alternatively at least partially control 1) the rate of one or more micro-structures and/or surface structures being exposed to a particular environment (e.g., fluids in a body passageway, gasses in the lungs, bile in a bile duct, air in the surrounding atmosphere, etc.), 2) the rate one or more micro-structures and/or surface structures degrades, dissolves and/or is absorbed, 3) the rate at which one or more biological agents are released from the one or more micro-structures and/or surface structures. The one or more coatings of protective material also or alternatively can be used to facilitate in the use of the medical device such as, but not limited to, 1) providing a smooth coating surface on at least a portion of the one or more micro-structures and/or surface structures, 2) providing a rough coating surface on at least a portion of the one or more micro-structures and/or surface structures, and/or 3) facilitating in one or more of the micro-structures and/or surface structures at least partially securing to, engaging with and/or penetrating into a body portion. As can be appreciated, the one or more coatings of protective material can be designed and/or formulated to have other and/or additional functions on the medical device.

Although, FIGS. 1-15 illustrate the medical device in the form of a stent for use in the cardiovascular field, the medical device can be used in other medical fields such as, but not limited to, orthopaedic field, cardiology field, pulmonology field, urology field, nephrology field, gastroenterology field, gynecology field, otolaryngology field or other surgical fields. As such, the medical device of the present invention can be in the form of surgical grafts sutures, staples, orthopaedic implants, bandages, nail, rod, screw, gels, micro or nano particles, vascular implant, a membrane surface, etc.). As can be appreciated, the medical device can take other forms. The medical device of the present invention can be used to addresses various medical problems such as, but not limited to, restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications, wounds, myocardial infarction, pulmonary thromboembolism, cerebral thromboembolism, thrombophlebitis, thrombocytopenia and/or bleeding disorders.

The medical device can be formed of a variety of materials such as, but not limited to, biodegradable polymers, biodegradable metals, other biodegradable materials, biostable polymers, biostable metals, other biolstable materials, or any combination thereof. The material or materials used to form the medical device include properties (e.g., strength, radial strength, tensile strength, longitudinal lengthening, heat sensitivity, biostability, biodegradability, biocapatability, etc.) that are selected to form a medical device which promotes the success of the medical device. The medical device can be made of one piece or multiple pieces. When the medical device is in the form of a stent, the stent can be expandable such as by a balloon and/or self expanding. The material that is used to form one or more portions of the medical device is typically selected to withstand the manufacturing process used to form the stent.

The medical device includes one or more surface structures, micro-structures and/or internal structures. Such structures can be formed by a variety of processes (e.g., machining, chemical modifications, chemical reactions, MEMS [e.g., micro-machining, etc.] etc.). These structures can be used to increase the bonding and/or adhesion of the biological agent, adhesive, marker material and/or polymer to the medical device, change the appearance or surface characteristics of the medical device, control the release rate of a biological agent, etc. The medical device itself can be formed by a variety of processes (e.g., machining, chemical modifications, chemical reactions, molding, extruding, laser cutting, MEMS [e.g., micro-machining, etc.], etc.). The techniques employed to deliver the medical device to a treatment area include, but are not limited to, angioplasty, vascular anastomoses, transplantation, implantation, subcutaneous introduction, minimally invasive surgical procedures, injection, topical applications, bolus administration, infusion, interventional procedures, and any combinations thereof. When the medical device is in the form of a surgical graft or stent, the medical device can be implanted or applied by techniques such as, but not limited to, suturing, staples, adhesive, anastomoses, balloon delivery, sheath catheter delivery, etc.

The stent illustrated in FIGS. 1-15 can be used in a body passageway such as a blood vessel. Such a stent is expandable to at least partially expanding occluded segments of a body passageway, but can be used for other or additional uses. For example, the expandable stent may be used for, but not limited to, such purposes as 1) a supportive stent placement within a blocked vasculature opened by transluminal recanalization, which are likely to collapse in the absence of an internal support; 2) forming a catheter passage through mediastinal and/or other veins occluded by inoperable cancers; 3) reinforcement of catheter created intrahepatic communications between portal and/or hepatic veins in patients suffering from portal hypertension; 4) supportive stent placement of narrowing of the esophagus, the intestine, the ureter and/or the urethra; and/or 5) supportive stent reinforcement of reopened and previously obstructed bile ducts. Accordingly, use of the term "stent" encompasses the foregoing or other usages within various types of body passageways, and also encompasses use for expanding a body passageway. In one specific non-limiting example, the stent can be used to open an obstructed blood vessel. The stent can include and/or be used with one or more biological agents used to inhibit thrombosis, in-stent restenosis, vascular narrowing and/or restenosis after the stent has been inserted into the blood vessel; however, this is not required. The one or more biological agents, when used, can also or alternatively be used to remove and/or dissolve lipids, fibroblast, fibrin, etc. from the blood vessel so as to at least partially clean the blood vessel of such substances in the region of the stent and/or down stream of the stent. As can be appreciated, the one or more biological agents, when used, can have additional or other functions.

As illustrated in FIG. 1, stent 20 is in the form of an expandable stent that includes at least one tubular shaped body member 30 having a first end 32, a second end 34, and member structures 36 disposed between the first and second ends. As can be appreciated, the stent can be formed of a plurality of body members connected together. Body member 30 has a first diameter which permits delivery of the body member into a body passageway. The first diameter of the body member is illustrated as substantially constant along the longitudinal length of the body member. As can be appreciated, the body member can have a varying first diameter along at least a portion of the longitudinal length of the body member. The body member also has a second expanded diameter, not shown. The second diameter typically varies in size; however, the second diameter can be non-variable in size. The stent can be expanded in a variety of ways such as by a balloon. A balloon expandable stent is typically pre-mounted or crimped onto an angioplasty balloon catheter. A balloon catheter is then positioned into the patient via a guide wire. Once the stent is properly positioned, the balloon catheter is inflated to the appropriate pressure for stent expansion. After the stent has been expanded, the balloon catheter is deflated and withdrawn, leaving the stent deployed at the treatment area. One or more surfaces of the stent can be treated so as to have generally smooth surfaces; however, this is not required. Generally, one or more ends of the stent are treated by filing, buffing, polishing, grinding, coating, and/or the like to remove or reduce the number of rough and/or sharp surfaces; however, this is not required. The smooth surfaces of the ends reduce potential damage to surrounding tissue as the stent is positioned in and/or expanded in a body passageway.

Referring again to FIGS. 1 and 2, the medical device includes a base material 40. The base material typically includes one or more metals and/or polymers. Non-limiting examples of polymers that can be used include parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof; however, other and/or additional metals can be used. Non-limiting examples of metals include aluminum, barium, bismuth, cobalt, copper, chromium, gold, iron, stainless steel, titanium, vanadium, nickel, zirconium, niobium, lead, molybdenum, platinum, yttrium, calcium, rare earth metals, rhenium, zinc, silver, depleted radioactive elements, tantalum and/or tungsten; however, other and/or additional metals can be used.

Figure 3:
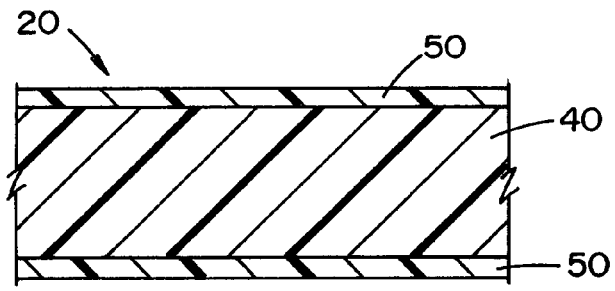
FIG. 3 is a cross-sectional view along line 2-2 of FIG. 1 illustrating a section that forms the stent that includes a polymer coating.

As illustrated in FIG. 3, the base material 40 can be coated with one or more biological agents and/or polymers that can be used to improve the functionality or success of the medical device. When a polymer coating is used, the polymer can be porous or non-porous polymers. Non-limiting examples of polymer that can be coated on the base material 40 include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof. As can be appreciated, other or additional polymers can be used. The polymer coating can have the same or different composition from the base material 40. Non-limiting examples of biological agent is coated on the base material 40 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, other or additional biological agents can also be used improve the functionality or success of the medical device. The amount of biological agent delivered to a certain region of a patient's body can be controlled by varying the type of biological agent, the coating thickness of the biological agent, the drug concentration of the biological agent, the solubility of the biological agent, the location the biological agent that is coated and/or impregnated on and/in the medical device, the amount of surface area of the medical device that is coated and/or impregnated with the biological agent, the location of the biological agent on the medical device, etc.; however, this is not required. One or more biological agents on and/or in the medical device can be controllably released and/or immediately released to optimize their effects and/or to compliment the function and success of the medical device. The controlled release can be accomplished by 1) controlling the size of the surface structures, micro-structures and/or internal structures in the medical device, 2) selecting a particular base material 40, and/or 3) using one or more polymer coatings; however, this is not required. The one or more biological agents can be combined with, or at least partially coated with, a polymer that affects the rate at which the biological agent is released from the medical device; however, this is not required. The polymer coating can also be used to assist in binding the one or more biological agents to the medical device; however, this is not required. The polymer coating can be biodegradable and/or biostable. The polymer coating can be formulated to form a bond with the biological agent to the stent; however, this is not required. The polymer used in the polymer coating and one or more biological agents can be mixed together prior to being applied to the medical device; however, this is not required. The one or more biological agents that are used in combination with a one or more polymers in the polymer coating 50 and/or base material 40 can control the release of the biological agent by molecular diffusion; however, this is not required. The thickness of the polymer coating 50 can be about 0.05-150 μm; however, other coating thickness can be used. The time period the one or more biological agents are released from the medical device can vary.

Figure 4:
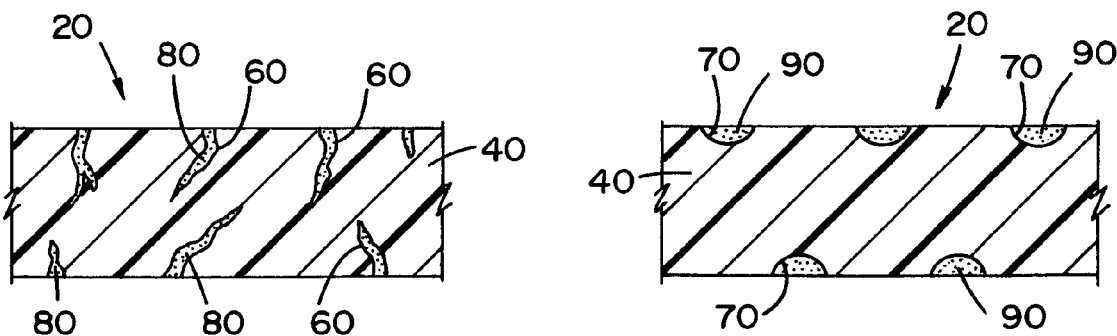
FIGS. 4 and 5 are a cross-sectional view along line 2-2 of FIG. 1 illustrating a section that forms the stent that includes a plurality of two types of pores and/or micro-pores in the section which are filled with one or more biological agents.
Figure 5:
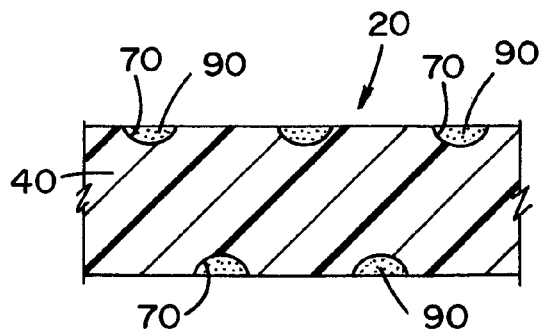

Referring now to FIG. 4, the base structure 40 of stent 20 includes a plurality of surface structures and/or micro-structures 60. The surface structures and/or micro-structures are illustrated as formed in the base structure of the stent. As defined herein, a micro-structure (e.g., micro-channel, micro-needle, micro-pore, etc.) is a structure that has at least one dimension (e.g., average width, average diameter, average height, average length, average depth, etc.) that is no more than about 2 mm, and typically no more than about 1 mm. The surface structures and/or micro-structures can be formed in the base material during the formation of the stent and/or from the surface treatment of the stent (e.g., etching, mechanical drill, etc.). In one non-limiting example, the stent is formed by MEMS technology and the surface structures and/or micro-structures are formed by MEMS technology. The surface structures and/or micro-structures are illustrated as in the form of pores in the base material. As can be appreciated, many other structures can be formed in the base material. For instance, as illustrated in FIG. 5, the surface structures and/or micro-structures are in the form of pits or depressions 70. As illustrated in FIGS. 4 and 5, the surface structures and/or micro-structures 60, 70 include one or more biological agents 80, 90; however, it can be appreciated that one or more surface structures and/or micro-structures can include a) a combination of polymer and biological agent, b) only a polymer, c) one biological agent, or d) nothing. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The size of the one or more surface structures and/or micro-structures can be used to at least partially control the rate of release of the biological agent and/or polymer from the one or more surface structures and/or micro-structures; however, this is not required. As can be appreciated, a layer that includes one or more biological agents or a combination of one or more biological agents and one or more polymers, not shown, can be coated in the surface of the base material; however, this is not required. This coating, if used, can include one or more of the same or one or more different biological agents from the one or more biological agents in the surface structures and/or micro-structures. As can also be appreciated, additional coatings of biological agent and/or polymer, not shown, can be used. The polymer, when used, can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer includes one or more non-porous polymers to at least partially control a rate of release by molecular diffusion of the one or more biological agents from stent 20. The one or more non-porous polymers can include, but are not limited to, parylene C, parylene N, parylene F and/or a parylene derivative.

Figure 12:
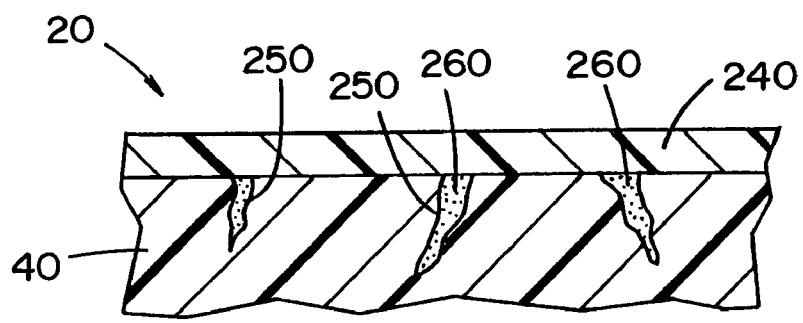
FIG. 12 is a cross-sectional view along line 2-2 of FIG. 1 illustrating a section that forms the stent that includes a plurality of two types of pores and/or micro-pores in the section which are filled with one or more biological agents and covered with one or more polymer coatings.

As illustrated in FIG. 12, a polymer layer 240 is coated on the top surface of the base material 40. The polymer layer 240 covers the one or more biological agents 260 located in the surface structures and/or micro-structures 250. The polymer layer can include one or more polymers. The polymer layer can include a porous polymer and/or non-porous polymer. The polymer layer can include one or more biological agent; however, this is not required. The polymer layer can include a biostable and/or biodegradable polymer. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer includes one or more non-porous polymers to at least partially control a rate of release by molecular diffusion of the one or more biological agents from stent 20. The one or more non-porous polymers can include, but are not limited to, parylene C, parylene N, parylene F and/or a parylene derivative. The biological agent can include, but is not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof.

Figure 6:
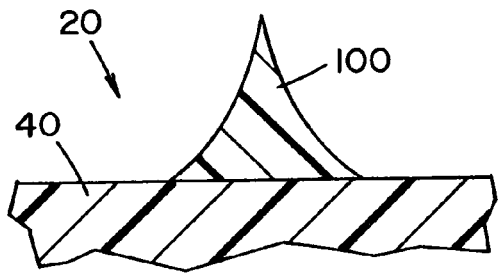
FIGS. 6 and 7 are a cross-sectional view along line 2-2 of FIG. 1 illustrating a section that forms the stent that includes a plurality of two types of micro-needles on the surface of the section which are formed of one or more polymers.
Figure 7:
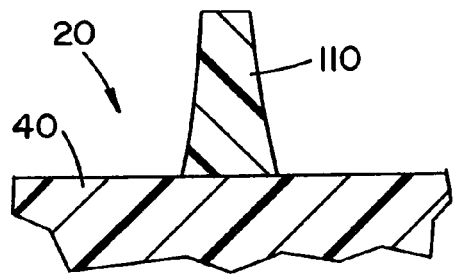
Figure 8:
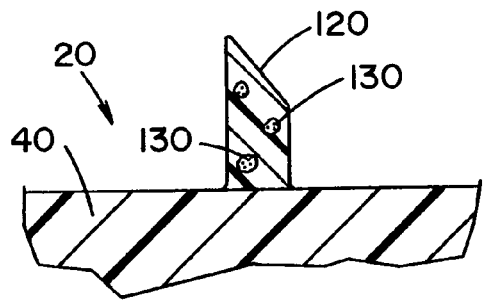
FIG. 8 is a cross-sectional view along line 2-2 of FIG. 1 illustrating a section that forms the stent that includes a plurality of another type of micro-needles on the surface of the section are formed of one or more polymer and biological agent.

Referring now to FIGS. 6-8, the base material 40 of stent 20 includes one or more needles or micro-needles 100, 110, 120 formed on the surface of the stent. These needles or micro-needles can be formed by MEMS (e.g., micro-machining, etc.) technology and/or by other processes. As illustrated in FIGS. 6-8, the needles or micro-needles can have a variety of shapes and sizes. The needles or micro-needles can be at least partially formed from one or more polymers and/or biological agents. It can be appreciated that the needles or micro-needles can be at least partially formed of other of additional material such as, but not limited to one or more adhesives, etc. As illustrated in FIG. 8, the needles or micro-needles include a combination of one or more polymers 120 and/or one or more biological agents 130. As can be appreciated, one or more layers of one or more biological agents and/or polymers can be coated on the needles or micro-needles; however, this is not required. When the one or more needles or micro-needles include and/or are coated with one or more biological agents, such biological agents can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The use of one or more biological agents to coat the top surface of the needles or micro-needles can provide a burst of biological agent in the interior of the blood vessel and/or the blood vessel itself during and/or after insertion of the stent.

Figure 9:
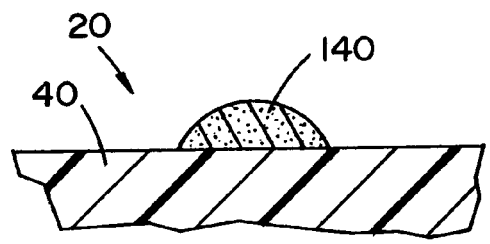
FIG. 9 is a cross-sectional view along line 2-2 of FIG. 1 illustrating a section that forms the stent that includes a plurality of another type of micro-structure on the surface of the section which are formed of one or more biological agents.

Referring now to FIG. 9, the base material 40 of stent 20 includes one or more surface structures or micro-structures 140 in the form of a mound; however, it can be appreciated that other or additional shapes can be used. The mound is formed on the surface of the stent. The mound can be formed by MEMS (e.g., micro-machining, etc.) technology and/or by other processes. The mound is shown to be formed of one or more biological agents; however, it can be appreciated that the mound can be formed of one or more polymers or a combination of one or more polymers and biological agents. As can also be appreciated, other or additional materials can be used to at least partially form the mound. The one or more biological agents can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however other or additional biological agents can be used. The one or more biological agents used to form the mound can provide a burst of biological agent in the interior of a body passageway and/or the body passageway itself during and/or after insertion of the stent in the body passageway; however, this is not required. As can be appreciated, a layer of one or more polymers can be coated on the mound; however, this is not required. The polymer layer can be used to control the release rate of the one or more biological agents from the mound; however, this is not required. The polymer layer can also or alternatively provide protection to the mound structure; however, this is not required. When the mound includes and/or is coated with one or more polymers, such polymers can include, but are not limited to, parylene, parylene C, parylene N, parylene F, PLGA, PEVA, PLA, PBMA, POE, PGA, PLLA, PAA, PEG, chitosan and/or derivatives of one or more of these polymers.

Figure 10:
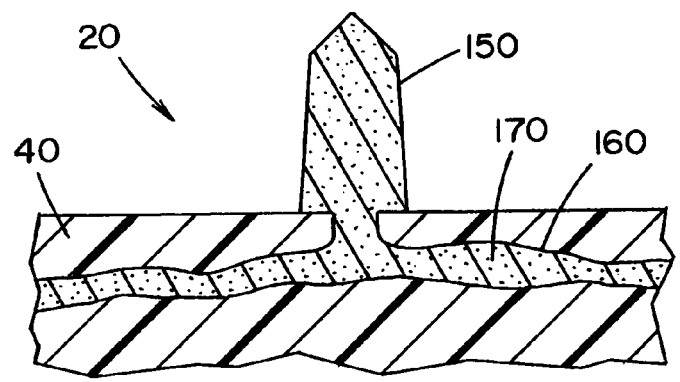
FIG. 10 is a cross-sectional view along line 2-2 of FIG. 1 illustrating a section that forms the stent that includes a plurality of another type of micro-needles on the surface of the section which are formed of one or more biological agents and which are interconnected to at least internal channels in the biodegradable material which is filled with one or more biological agents.
Figure 11:
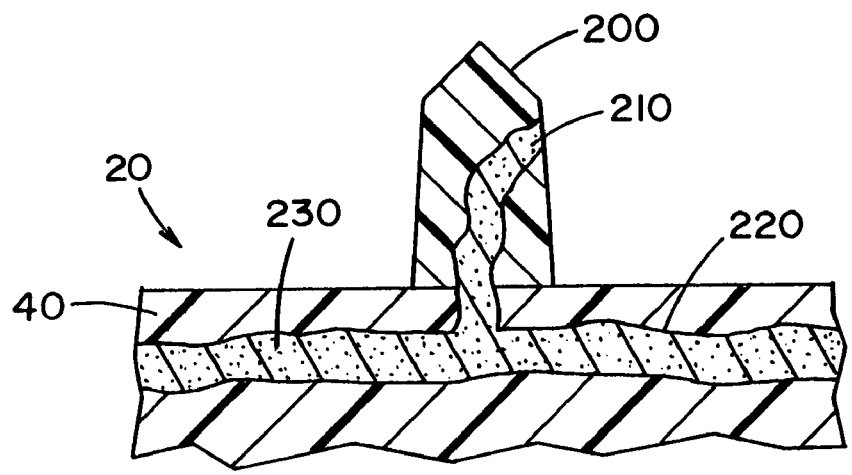
FIG. 11 is a cross-sectional view along line 2-2 of FIG. 1 illustrating a section that forms the stent that includes a plurality of another type of micro-needles on the surface of the section which are formed of one or more polymers and which the micro-needles include a channel filled with one or more biological agents and which channel in the micro-needle is interconnected to at least internal channel in the section which is filled with one or more biological agents.
Figure 13:
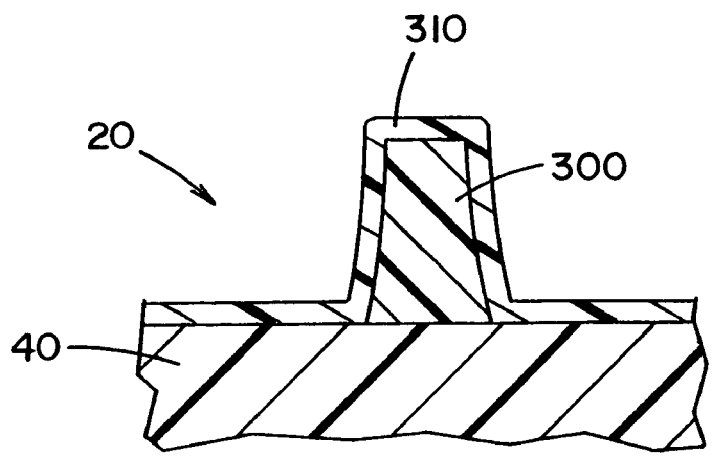
FIG. 13 is a cross-sectional view along line 2-2 of FIG. 1 illustrating micro-needles on the surface of the stent that is formed of one or more polymers and coated with one or more polymers.

Referring now to FIGS. 10, 11 and 13, the base material 40 of stent 20 includes one or more needles or micro-needles 150, 200, 300. These needles or micro-needles can be formed by MEMS (e.g., micro-machining, etc.) technology and/or by other processes. The one or more needles or micro-needles are formed on the surface of the stent. The one or more needles or micro-needles can formed from one or more biological agents, polymers, and/or adhesives. The polymer can be porous, non-porous, biodegradable and/or biostable. Polymers that can be used to at least partially form the one or more needles or micro-needles include, but are not limited to, Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. Non-limiting examples of one or more biological agents that can be used can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however other or additional biological agents can be used.

Referring again to FIG. 10, the needle or micro-needle is formed over on opening in the surface of the base material which opening is connected to an internal structure 160 in the base material. The internal structure is shown to be a channel; however, other or additional internal structures can be included in the base material. These internal structures can be formed by MEMS (e.g., micro-machining, etc.) technology and/or by other processes. The internal structure 160 is shown to be filled with one or more biological agents 170; however, it can be appreciated that the internal structures can include other or additional materials (e.g., polymers, adhesive, etc.); however, this is not required. As can also be appreciated, the internal structures can be partially or fully empty of any type of material; however, this is not required. The one or more biological agents 170 in the internal structure 160 can be the same or different from the one or more biological agents that at least partially form the one or more needles or micro-needles 150.

Referring again to FIG. 11, the needle or micro-needle includes a channel that is filled with one or more biological agents. As can be appreciated, other or additional materials can be included in the channel in the one or more needles or micro-needles (e.g., polymer, adhesive, etc.). As can be appreciated, a layer of one or more polymers can be coated on the one or more needles or micro-needles; however, this is not required. The polymer layer can be used to control the release rate of the one or more biological agents from the one or more needles or micro-needles; however, this is not required. The polymer layer can also or alternatively provide protection to the structure of the one or more needles or micro-needles; however, this is not required. When the one or more needles or micro-needles include and/or are coated with one or more polymers, such polymers can include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof. The surface of the one or more needles or micro-needles can include a layer of one or more biological agents to provide a burst of biological agent in the interior of the blood vessel and/or the blood vessel itself during and/or after insertion of the stent; however, this is not required. The channel 210 in the one or more needles or micro-needles 200 are shown to be connected to an opening in the surface of the base material which opening is connected to an internal structure 220 in the base material. The internal structure is shown to be a channel; however, other or additional internal structures can be included in the base material. These internal structures can be formed by MEMS (e.g., micro-machining, etc.) technology and/or by other processes. The internal structure 220 is shown to be filled with one or more biological agents 230; however, it can be appreciated that the internal structures can include other or additional materials (e.g., polymers, adhesive, etc.); however, this is not required. As can also be appreciated, the internal structures can be partially or fully empty of any type of material; however, this is not required. The one or more biological agents 230 in the internal structure 220 can be the same or different from the one or more biological agents 210 in the channel of the one or more needles or micro-needles 200.

Referring again to FIG. 13, a polymer layer or layer of biological agent 310 is coated on the top of the one or more needles or micro-needles. The one or more polymers/biological agents that form coating 310 can be the same or different from the one or more polymers that form the one or more needles or micro-needles 300. The polymer/biological agent layer can be used to provide protection to the structure of the one or more needles or micro-needles 300. The surface of the coating 310 can include a layer of one or more biological agents to provide a burst of biological agent in the interior of the blood vessel and/or the blood vessel itself during and/or after insertion of the stent; however, this is not required.

Figure 14:
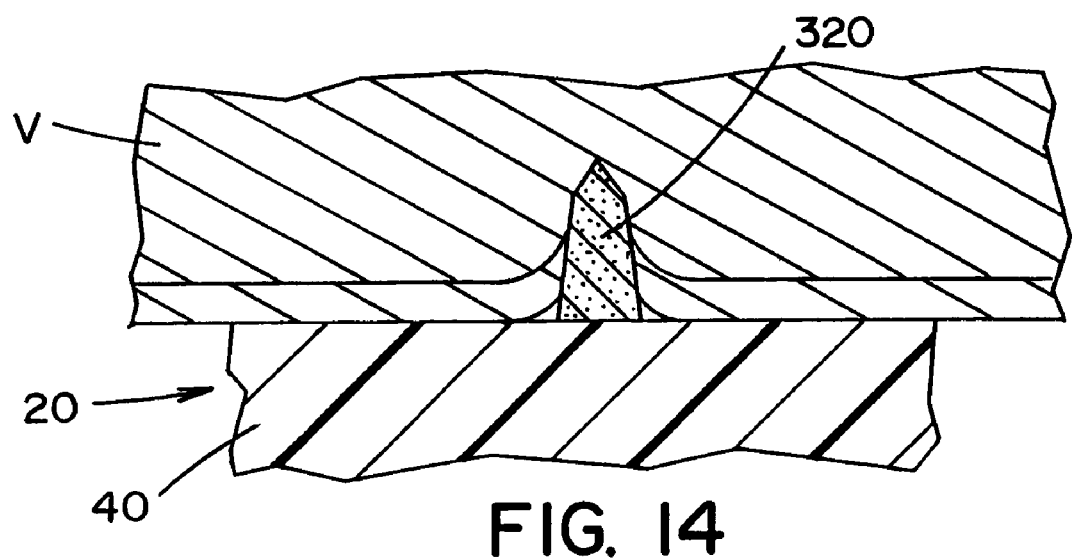
FIG. 14 is a cross-sectional view of a micro-needle on a stent that is penetrating into the inner surface of a blood vessel.

Referring now to FIG. 14, there is illustrated an enlarged portion of a surface of a stent 20 which includes a surface needle, micro-needle or other type of structure or microstructure 320. The needle is shown to include at least one biological agent; however, the needle can also or alternatively include one or more polymers, adhesives, etc. The stent, when in the form of a stent, is illustrated as in an expanded state. When the stent is inserted or expanded in a treatment area, the needle 320 on the outer surface of the stent engages and/or at least partially penetrates into blood vessel or organ V. When the needle includes one or more biological agents, the one or more biological agents are at least partially locally applied to a treatment area. This can be a significant advantage over system-wide treatment with one or more biological agents. The local treatment with one or more biological agent via the needle can more effectively and/or efficiently direct the desired agents to a treated area. The release of one or more biological agents from the needle can be controlled, if desired, to direct the desired amount of one or more biological agents to a treated area over a desired period of time. When the stent is expanded in a blood vessel, the one or more needles enable local delivery of one or more biological agents into the wall of the blood vessel. This local delivery is especially advantageous in large and/or thick blood vessels wherein system wide drug treatment is not very effective. In addition, the local delivery of biological agent by the needle directly into the blood vessel can be more effective than only releasing the biological agent from the surface of the stent since diffusion from the surface of the stent to the larger and/or thicker blood vessel may not be as effective as direct delivery by the needles to the blood vessel. The one or more needles on the stent surface can also or alternatively be used to facilitate in securing the stent to the treatment area during the expansion and/or insertion of the stent in a treatment area.

Figure 15:
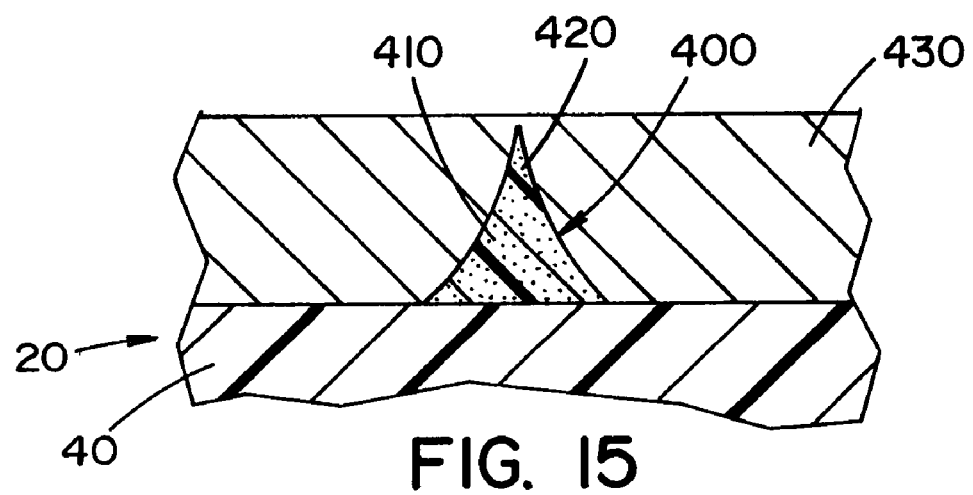
FIG. 15 is a cross-sectional view of a micro-needle on a stent that is fully embedded in a protective material.

Referring now to FIG. 15, there is illustrated an enlarged portion of a surface of a stent 20 which includes a micro-needle or other type of micro-structure 400. The micro-needle is shown to include at least one polymer 410 and at least one biological agent 420; however, the micro-needle could be formed solely of polymer or solely of biological agent. As can be appreciated, the micro-needle can have other forms such as, but not limited to the form illustrated in FIGS. 6-11, 13 and 14. The micro-needle is illustrated as fully embedded in a protective coating 430; however, it can be appreciated that the micro-needle can be only partially embedded in the protective coating. The protective coating can be designed to fully protect the micro-needle as the stent is inserted in the body passageway. The protective material 430 can be formed of a biodegradable material so as to allow the micro-needle to be exposed to the body passageway; however, this is not required. The release of one or more biological agents from the micro-needle can be controlled by the protective coating; however, this is not required. The thickness of the protective material 430 is illustrated as being generally uniform relative to the base material 40 of stent 20. FIG. 14 illustrates the thickness of the protective material 430 as being generally non-uniform relative to the base material 40 of stent 20. FIGS. 14 and 15 also illustrate that the thickness of the protective material 430 as being generally non-uniform relative to different regions of micro-structure 400. For instance, the thickness of protective material 430 is less at the top tip of micro-structure 400 as opposed to the other regions of micro-structure 400 as illustrated in both FIGS. 14 and 15.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A medical device having a body portion that includes a plurality of micro-structures connected to said body portion, said medical device is a stent, sheath, or balloon, at least a portion of said micro-structures includes a plurality of micro-needles that extend upwardly from an outer surface of said body portion, said protective material coated on said outer surface of said medical device and said plurality of micro-needles, said protective coating at least partially embedding said plurality of micro-needles in said protective coating so as to protect said plurality of micro-needles from damage prior to positioning said medical device at a treatment location, said protective material formed of a biodegradable material, said protective material formed of a different material composition than said plurality of micro-needles and said outer surface of said medical device, said plurality of micro-needles having a shape and size designed to penetrate into a treatment location of a body passageway when said body portion is expanded to an expanded cross-sectional area.

2. The medical device as defined in claim 1, wherein at least a portion of said medical device is formed by MEMS technology.

3. The medical device as defined in claim 1, wherein at least one region of said medical device includes at least one biological agent.

4. The medical device as defined in claim 3, wherein said at least one biological agent includes one or more compounds selected from the group consisting of trapidil, trapidil derivatives, taxol, taxol derivatives, cytochalasin, cytochalasin derivatives, paclitaxel, paclitaxel derivatives, rapamycin, rapamycin derivatives, GM-CSF, and GM-CSF derivatives.

5. The medical device as defined in claim 3, wherein at least one region of said medical device includes at least one polymer to at least partially coat said at least biological agent, at least partially encapsulate said at least biological agent, or at least partially coat and encapsulate said at least biological agent.

6. The medical device as defined in claim 5, wherein said at least one polymer is designed to controllably release at least one of said biological agents when said medical device is positioned in the body passageway.

7. The medical device as defined in claim 5, wherein said at least one polymer includes one or more polymers selected from the group consisting of parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and a PEG derivative.

8. The medical device as defined in claim 1, wherein said at least one micro-structure is at least partially formed by MEMS technology.

9. The medical device as defined in claim 1, wherein said plurality of micro-needles is at least partially formed of one or more materials, at least partially includes one or more materials, or at least partially includes and is at least partially formed of one or more materials, said one or more materials selected from the group consisting of a polymer, and a biological agent.

10. The medical device as defined in claim 1, wherein said medical device includes at least one internal structure, said internal structure including one or more materials selected from the group consisting of a polymer, and a biological agent.

11. The medical device as defined in claim 1, wherein said protective material at least partially controls a release rate of one or more materials from a plurality of said micro-needles.

12. A medical device that includes a body potion, said body portion includes a plurality of micro-structures, said medical device being a stent or a sheath, at least one region of said medical device includes biological agent, at least one region of said medical device includes polymer to a) at least partially coat said biological agent, b) at least partially encapsulate said biological agent, or c) at least partially coat and encapsulate said biological agent, at least a portion of said micro-structures connected to and extending upwardly from an outer surface of said body portion, said micro-structures extending upwardly from said outer surface of said body portion a distance of no more than 2 mm, said protective material formed of a different material composition than said outer surface of said medical device and said plurality of micro-structures extending upwardly from said outer surface of said body portion, said protective material coated on said outer surface of said medical device and said plurality of micro-structures extending upwardly from said outer surface of said body portion, said protective coating at least partially embedding said plurality of micro-structures extending upwardly from said outer surface of said body portion in said protective coating so as to at least partially protect said plurality of micro-structures from damage prior to positioning said medical device at a treatment location, said plurality of said micro-structures that extends upwardly from said outer surface of said body portion is i) at least partially formed of one or more materials, ii) at least partially includes one or more materials, or iii) at least partially includes and is at least partially formed of one or more materials, said one or more materials selected from the group consisting of said polymer and said biological agent, said plurality of said micro-structures that extends upwardly from said outer surface of said body portion coated with or including said biological agent, said plurality of micro-structures that extends upwardly from said outer surface of said body portion having a shape and size designed to penetrate into a treatment location of a body passageway when said body portion is expanded to an expanded cross-sectional area and to deliver said biological agent in said penetrated region of said body passageway, said biological agent including one or more compounds selected from the group consisting of trapidil, trapidil derivatives, taxol, taxol derivatives, cytochalasin, cytochalasin derivatives, paclitaxel, paclitaxel derivatives, rapamycin, rapamycin derivatives, GM-CSF, and GM-CSF derivatives, said polymer including one or more polymers selected from the group consisting of parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and a PEG derivative.

13. The medical device as defined in claim 12, wherein said plurality of said micro-structures that extends upwardly from said outer surface of said body portion includes micro-needles.

14. The medical device as defined in claim 12, wherein said protective material at least partially controls a release rate of one or more materials from at least one of said micro-structures.

15. The medical device as defined in claim 13, wherein said protective material at least partially controls a release rate of one or more materials from at least one of said micro-needles.

16. The medical device as defined in claim 12, wherein said biological agent is included in or coated on said plurality of said micro-structures that extends upwardly from said outer surface of said body portion, said biological agent includes rapamycin or rapamycin derivatives.

17. The medical device as defined in claim 15, wherein said biological agent is included in or coated on said plurality of said micro-structures that extends upwardly from said outer surface of said body portion, said biological agent includes rapamycin or rapamycin derivatives.

18. The medical device as defined in claim 12, wherein said at least one polymer includes poly(lactic acid) or poly(lactic acid) derivatives.

19. The medical device as defined in claim 17, wherein said at least one polymer includes poly(lactic acid) or poly(lactic acid) derivatives.

20. The medical device as defined in claim 12, wherein said protective material is biodegradable.

21. The medical device as defined in claim 19, wherein said protective material is biodegradable.

22. A medical device for use in a body passageway, said medical device including a stent having a body potion, an outer surface of said body portion including a plurality of micro-structures, at least a portion of micro-structures extending upwardly from said outer surface of said body portion, said micro-structures that extend upwardly from said outer surface of said body portion extending no more than about 2 mm upwardly from said outer surface of said body portion, said protective material also coated on said outer surface of said body portion, said protective material at least partially embedding said plurality of micro-structures extending upwardly from said outer surface of said body portion in said protective coating so as to protect said plurality of micro-structures that extend upwardly from said outer surface of said body portion from damage prior to positioning said medical device at a treatment location of the body passageway, said protective material designed and formulated to enable said plurality of micro-structures to at least partially breaks from or penetrates through said protective coating when said stent is expanded, said protective material is a biodegradable material, said protective material formed of a different material composition than outer surface of said medical device and said plurality of micro-structures extending upwardly from said outer surface of said body portion, said protective material including one or more materials selected from the group consisting of a first biological agent, adhesive, sugar, carbohydrate compound, paraffin, starch and salt, said plurality of micro-structures that extend upwardly from said outer surface of said body portion are fully formed of one or more materials selected from the group consisting of said polymer and biological agent, said plurality of said micro-structures that extend upwardly from said outer surface of said body portion coated with or including said biological agent, said plurality of micro-structures that extend upwardly from said outer surface of said body portion having a shape and size designed to penetrate into said treatment location of said body passageway when said body portion is expanded to an expanded cross-sectional area and to deliver said biological agent in said penetrated region of said body passageway, said biological agent including one or more compounds selected from the group consisting of trapidil, trapidil derivatives, taxol, taxol derivatives, cytochalasin, cytochalasin derivatives, paclitaxel, paclitaxel derivatives, rapamycin, rapamycin derivatives, GM-CSF, and GM-CSF derivatives, said polymer including one or more polymers selected from the group consisting of parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and a PEG derivative.

23. The medical device as defined in claim 22, wherein said plurality of said micro-structures extending upwardly from said outer surface of said body portion are micro-needles, a plurality of said micro-needles includes polymer and biological agent.

24. The medical device as defined in claim 22, wherein said plurality of said micro-structures extend upwardly from said outer surface of said body portion a distance of at least about 15 µm and no more than about 400 µm.

25. The medical device as defined in claim 23, wherein a plurality of said micro-structures extend upwardly from said outer surface of said body portion a distance of at least about 15 μm and no more than about 400 μm.

26. The medical device as defined in claim 22, wherein said plurality of said micro-structures include trapidil, trapidil derivatives, GM-CSF, GM-CSF derivatives, or combinations thereof.

27. The medical device as defined in claim 25, wherein said plurality of said micro-structures include trapidil, trapidil derivatives, GM-CSF, GM-CSF derivatives, or combinations thereof.

28. The medical device as defined in claim 27, wherein said plurality of said micro-structures extend upwardly from said outer surface of said body portion a distance of about 15-250 μm.

29. The medical device as defined in claim 22, wherein said protective material controls a release rate of said biological agent from said plurality of said micro-structures that extend upwardly from said outer surface of said body portion.

30. The medical device as defined in claim 23, wherein said protective material controls a release rate of said biological agent from said plurality of said micro-needles.

31. The medical device as defined in claim 28, wherein said protective material controls a release rate of said biological agent from said plurality of said micro-needles.

32. The medical device as defined in claim 1, wherein said protective material having a coating thickness that is generally uniform on said outer surface of said body portion, said coating thickness of said protective material on said various regions of said plurality of micro-needles being non-uniform.

33. The medical device as defined in claim 32, wherein said coating thickness of protective material is a thickness that results in said plurality of micro-needles being fully embedded in said protective material.

34. The medical device as defined in claim 12, wherein said protective material having a coating thickness that is generally uniform on said outer surface of said body portion, said coating thickness of said protective material on said various regions of said plurality of micro-structures extending upwardly from said outer surface of said body portion being non-uniform.

35. The medical device as defined in claim 21, wherein said protective material having a coating thickness that is generally uniform on said outer surface of said body portion, said coating thickness of said protective material on said various regions of said plurality of micro-structures extending upwardly from said outer surface of said body portion being non-uniform.

36. The medical device as defined in claim 34, wherein said coating thickness of protective material is a thickness that results in said plurality of micro-structures extending upwardly from said outer surface of said body portion being fully embedded in said protective material.

37. The medical device as defined in claim 35, wherein said coating thickness of protective material is a thickness that results in said plurality of micro-structures extending upwardly from said outer surface of said body portion being fully embedded in said protective material.

38. The medical device as defined in claim 22, wherein said protective material having a coating thickness that is generally uniform on said outer surface of said body portion, said coating thickness of said protective material on said various regions of said plurality of micro-structures extending upwardly from said outer surface of said body portion being non-uniform.

39. The medical device as defined in claim 31, wherein said protective material having a coating thickness that is generally uniform on said outer surface of said body portion, said coating thickness of said protective material on said various regions of said plurality of micro-structures extending upwardly from said outer surface of said body portion being non-uniform.

40. The medical device as defined in claim 38, wherein said coating thickness of protective material is a thickness that results in said plurality of micro-structures extending upwardly from said outer surface of said body portion being fully embedded in said protective material.

41. The medical device as defined in claim 39, wherein said coating thickness of protective material is a thickness that results in said plurality of micro-structures extending upwardly from said outer surface of said body portion being fully embedded in said protective material.

42. The medical device as defined in claim 1, wherein said protective material is designed and formulated to enable said plurality of micro-structures to at least partially break from or penetrate through said protective coating when said stent is expanded, said protective material including one or more materials selected from the group consisting of a first biological agent, adhesive, sugar, carbohydrate compound, paraffin, starch and salt.

43. The medical device as defined in claim 12, wherein said protective material is designed and formulated to enable said plurality of micro-structures to at least partially break from or penetrate through said protective coating when said stent is expanded, said protective material including one or more materials selected from the group consisting of a first biological agent, adhesive, sugar, carbohydrate compound, paraffin, starch and salt.

44. The medical device as defined in claim 38, wherein said protective material is designed and formulated to enable said plurality of micro-structures to at least partially break from or penetrate through said protective coating when said stent is expanded, said protective material including one or more materials selected from the group consisting of a first biological agent, adhesive, sugar, carbohydrate compound, paraffin, starch and salt.

* * * * *